United States Patent
Xu et al.

(10) Patent No.: US 10,327,650 B2
(45) Date of Patent: Jun. 25, 2019

(54) DEVICES AND SYSTEMS FOR REAL-TIME RECOGNITION OF RESTORATION OF SPONTANEOUS CIRCULATION (ROSC) IN CARDIO-PULMONARY RESUSCITATION (CPR) PROCESS

(71) Applicants: Peking Union Medical College Hospital, Chinese Academy of Medical Sciences, Beijing (CN); SHENZHEN MINDRAY BIO-MEDICAL ELECTRONICS CO., LTD., Shenzhen (CN)

(72) Inventors: Jun Xu, Beijing (CN); Xuezhong Yu, Beijing (CN); Fei Han, Shenzhen (CN); Liangliang Zheng, Beijing (CN); Cheng Wang, Shenzhen (CN); Xiaocui Zhang, Shenzhen (CN); Chen Li, Beijing (CN); Jingming Yang, Shenzhen (CN); Xingliang Jin, Shenzhen (CN); Yangyang Fu, Beijing (CN); Dongqi Yao, Beijing (CN)

(73) Assignees: PEKING UNION MEDICAL COLLEGE HOSPITAL, Beijing (CN); SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 572 days.

(21) Appl. No.: 14/462,418

(22) Filed: Aug. 18, 2014

(65) Prior Publication Data
US 2015/0164339 A1 Jun. 18, 2015

(30) Foreign Application Priority Data
Dec. 16, 2013 (CN) .......................... 2013 1 0685817

(51) Int. Cl.
A61B 5/026 (2006.01)
A61B 5/024 (2006.01)
(Continued)

(52) U.S. Cl.
CPC .............. *A61B 5/024* (2013.01); *A61B 5/026* (2013.01); *A61B 5/02416* (2013.01);
(Continued)

(58) Field of Classification Search
CPC .......... A61H 2230/06; A61H 2230/065; A61H 31/005; A61H 2230/045; A61H 2230/04;
(Continued)

(56) References Cited

U.S. PATENT DOCUMENTS

| 4,628,939 A | * 12/1986 | Little .................. A61B 5/0404 600/509 |
| 2004/0267324 A1 | 12/2004 | Geheb et al. |

(Continued)

FOREIGN PATENT DOCUMENTS

| WO | WO 2012166568 A2 * 12/2012 | ......... G06F 19/3406 |
| WO | WO 2013181376 A1 * 12/2013 | ........... A61B 5/0205 |

OTHER PUBLICATIONS

Bruel and Kjaer, PSD (Power spectral density)—description, http://www.bksv.com/ServiceCalibration/Support/Faq/Items/PSDPowerspectraldensitydescription.*

*Primary Examiner* — LaToya M Louis
(74) *Attorney, Agent, or Firm* — Kory D. Christensen

(57) ABSTRACT

This disclosure relates to methods, devices and systems for real-time recognition of restoration of spontaneous circulation (ROSC) in the cardio-pulmonary resuscitation (CPR) process. Recognition mechanisms in both time domain and frequency domain are provided for the ROSC recognition, where the time-domain recognition logic may detect the ROSC by recognizing envelope features of sampled signals (Continued)

in the time domain, and the frequency-domain recognition logic may detect the ROSC by recognizing spectral peaks at different frequency points continuously or significant variations of amplitude of spectral peaks in the frequency spectrum.

15 Claims, 31 Drawing Sheets

(51) Int. Cl.
*A61H 31/00* (2006.01)
*A61B 5/1455* (2006.01)
*A61B 5/00* (2006.01)

(52) U.S. Cl.
CPC ........ *A61B 5/14551* (2013.01); *A61B 5/7235* (2013.01); *A61B 5/7282* (2013.01); *A61H 31/00* (2013.01); *A61H 31/005* (2013.01); *A61B 2505/01* (2013.01); *A61H 2230/04* (2013.01); *A61H 2230/207* (2013.01)

(58) Field of Classification Search
CPC ........ A61H 2230/207; A61H 2230/208; A61B 5/048; A61B 5/04014; A61B 5/7235
See application file for complete search history.

(56) References Cited

U.S. PATENT DOCUMENTS

| | | | |
|---|---|---|---|
| 2006/0149144 A1 | 7/2006 | Lynn et al. | |
| 2007/0213619 A1* | 9/2007 | Linder | A61B 5/02416 600/481 |
| 2012/0016179 A1* | 1/2012 | Paradis | A61H 9/0078 600/17 |
| 2013/0338724 A1* | 12/2013 | Joo | A61N 1/3987 607/3 |

* cited by examiner

0° phase deviation

90° phase deviation

180° phase deviation

270° phase deviation

0° phase deviation

90° phase deviation

180° phase deviation

270° phase deviation

DEVICES AND SYSTEMS FOR REAL-TIME RECOGNITION OF RESTORATION OF SPONTANEOUS CIRCULATION (ROSC) IN CARDIO-PULMONARY RESUSCITATION (CPR) PROCESS

CROSS-REFERENCE

This application claims benefit and advantages of Chinese Patent Application No. 201310685817.2, filed Dec. 16, 2013, which is hereby incorporated by reference.

TECHNICAL FIELD

This disclosure generally relates to recognition of restoration of spontaneous circulation (ROSC), and in particular relates to devices for real-time recognition of ROSC in the cardio-pulmonary resuscitation (CPR) process, ROSC recognition and post-ROSC circulation quality evaluation systems, and ROSC feedback systems in the CPR process.

BACKGROUND

Cardiovascular disease, the major manifestation of which is sudden cardiac death (SCD), has become the top cause of death. Cardiopulmonary resuscitation (CPR) is universally acknowledged to be the most effective method to rescue patients from cardiac arrest. Given to the fact that evidence has accumulated that even short interruptions in CPR are harmful, the 2010 American Heart Association Guidelines for CPR and Emergency Cardiovascular Care puts an emphasis on immediately resuming CPR after shock delivery rather than evaluating the restoration of spontaneous circulation (ROSC). However, this recommendation neglects the problem of interference between the spontaneous circulation and the chest compression in patients who had ROSC, which may disturb hemodynamics and exacerbate the damage to the heart that could cause heart arrest. There is thus a need to develop a rapid and exact recognition system of ROSC in the CPR process to avoid this problem.

SUMMARY OF THIS DISCLOSURE

Spontaneous circulation recognition systems can be established based on the theory of pulse oximetry waveform analysis, which would make it easy to recognize ROSC during CPR. These systems may help doctors determine when to stop CPR in time and increase CPR effectiveness.

In this disclosure, for the purpose of assisting in a doctor's clinical decisions, ROSC in the CPR process can be recognized based on arterial pulse oximetry technology and in combination with clinical physiological characteristics and digital signal processing methods.

In one aspect, an ROSC recognition device for real-time recognition of ROSC in the CPR process can include a signal acquisition apparatus and a signal analysis apparatus. The signal acquisition apparatus can be used to acquire pulse oximetry waveform signals of a patient. The signal analysis apparatus can be used to analyze these signals to determine whether there is ROSC in the CPR process in real time.

In some embodiments, the signal analysis apparatus can include time-domain recognition logic and/or frequency-domain recognition logic. The time-domain recognition logic can determine whether there is ROSC in the CPR process by detecting envelope features of the signals in the time domain, and the frequency-domain recognition logic can determine whether there is ROSC in the CPR process by detecting time-varying features of spectral peaks of the signals in the frequency domain.

In some embodiments, the time-domain recognition logic can determine that there is ROSC when continuous and regular envelope features are recognized.

In some embodiments, the frequency-domain recognition logic can determine that there is ROSC when spectral peaks are recognized continuously at different frequencies or significant amplitude change is recognized for spectral peaks within a certain period.

In some embodiments, the signal acquisition apparatus may acquire the pulse oximetry waveform signals of the patient by red light and/or infrared light.

In another aspect, an ROSC recognition and post-ROSC circulation quality evaluation system can include the above-described ROSC recognition device and a post-ROSC circulation quality evaluation apparatus for evaluating post-ROSC circulation quality.

In some embodiments, the post-ROSC circulation quality evaluation apparatus can evaluate the post-ROSC circulation quality based on variations of cardiac stroke volume within a certain period.

In some embodiments, after the ROSC recognition device has determined there is ROSC, the post-ROSC circulation quality evaluation apparatus can calculate area characteristics of AC components of pulse signals sampled by the ROSC recognition device to evaluate the stroke volume variations under spontaneous cardiac rhythm to reflect the post-ROSC dynamic quality.

In some embodiments, the post-ROSC circulation quality evaluation apparatus can evaluate the post-ROSC circulation quality based on variations of pulse rate.

In still another aspect, an ROSC feedback system in a CPR process can include an ROSC recognition and post-ROSC circulation quality evaluation apparatus and a CPR apparatus. The ROSC recognition and post-ROSC circulation quality evaluation apparatus may be used for real-time recognition of ROSC in the CPR process and for post-ROSC circulation quality evaluation. The CPR apparatus may provide compression output to a patient. Upon detection of the ROSC, the ROSC recognition and post-ROSC circulation quality evaluation apparatus can control the CPR apparatus to stop the compression output, and can start the post-ROSC circulation quality evaluation. When the post-ROSC circulation quality is evaluated to be unstable, the ROSC recognition and post-ROSC circulation quality evaluation apparatus can control the CPR apparatus to restart the compression output and can restart the real-time recognition of ROSC.

In some embodiments, the ROSC recognition and post-ROSC circulation quality evaluation apparatus can include time-domain recognition logic and/or frequency-domain recognition logic. The time-domain recognition logic can determine whether there is ROSC in the CPR process by detecting time envelope features of sampled signals in the time domain, and the frequency-domain recognition logic can determine whether there is ROSC in the CPR process by detecting time-varying features of spectral peaks of the sampled signals in the frequency domain.

In some embodiments, the time-domain recognition logic can determine that there is ROSC when continuous and regular envelope features are recognized.

In some embodiments, the frequency-domain recognition logic can determine that there is ROSC when spectral peaks are recognized continuously at different frequencies or significant amplitude change is recognized for spectral peaks within a certain period.

In yet another aspect, an ROSC feedback system in a CPR process can include an ROSC recognition and post-ROSC circulation quality evaluation apparatus, a CPR apparatus and a CPR quality evaluation apparatus. The ROSC recognition and post-ROSC circulation quality evaluation apparatus may be used for real-time recognition of ROSC in the CPR process and for post-ROSC circulation quality evaluation. The CPR apparatus may provide compression output to a patient. The CPR quality evaluation apparatus may be used to evaluate CPR quality. Upon detection of the ROSC, the ROSC recognition and post-ROSC circulation quality evaluation apparatus can control the CPR apparatus to stop the compression output, and can start the post-ROSC circulation quality evaluation. When the post-ROSC circulation quality is evaluated to be unstable, the ROSC recognition and post-ROSC circulation quality evaluation apparatus can control the CPR apparatus to restart the compression output, and can restart the real-time recognition of ROSC. While the CPR apparatus is providing the compression output, the CPR apparatus can interact with the CPR quality evaluation apparatus so that the CPR quality evaluation apparatus can recognize the CPR compression state and provide feedback to the CPR apparatus to achieve an optimal compression output.

In some embodiments, the ROSC recognition and post-ROSC circulation quality evaluation apparatus can include time-domain recognition logic and/or frequency-domain recognition logic. The time-domain recognition logic can determine whether there is ROSC in the CPR process by detecting time envelope features of sampled signals in the time domain, and the frequency-domain recognition logic can determine whether there is ROSC in the CPR process by detecting time-varying features of spectral peaks of the sampled signals in the frequency domain.

In some embodiments, the time-domain recognition logic can determine that there is ROSC when continuous and regular envelope features are recognized.

In some embodiments, the frequency-domain recognition logic can determine that there is ROSC when spectral peaks are recognized continuously at different frequencies or significant amplitude change is recognized for spectral peaks within a certain period.

In still another aspect, an ROSC recognition device without external compression after defibrillation can include a signal acquisition device and a signal analysis device. The signal acquisition apparatus can be used to acquire pulse wave signals of a patient. The signal analysis apparatus can be used to analyze these signals to determine whether there is ROSC after defibrillation in real time.

In some embodiments, the signal acquisition apparatus can acquire the pulse wave signals of the patient by red light and/or infrared light.

In some embodiments, the signal analysis apparatus can perform real-time filtering on the signals by a band pass filter before analysis to eliminate noise interference beyond the physiological frequency band.

In some embodiments, the signal analysis apparatus can establish a sliding time window for the signals, and then determine whether there is a pulse feature within the sliding time window.

In some embodiments, the signal analysis apparatus can determine that there is ROSC after defibrillation when the pulse wave number in the sliding time window exceeds a threshold number, and the quality of a single pulse wave exceeds a threshold quality.

In some embodiments, the quality of the single pulse wave can be determined by its amplitude, width and shape.

In some embodiments, a time duration of the sliding time window can be adaptively adjusted according to frequencies of the pulse wave.

Through the above-described devices and systems, a doctor can know whether a patient has restored his/her spontaneous circulation in a compression interval or even in the continuous compression process, and thus the doctor can make clinical decisions in real time to avoid potential damage on the circulation system and other systems of the patient with ROSC by the external compression.

These and other features and advantages of this disclosure can be understood more thoroughly according to the following descriptions in combination with the accompanying drawings of respective embodiments.

BRIEF DESCRIPTION OF THE DRAWINGS

The detailed descriptions of respective embodiments in this disclosure can be understood better when combined with the following figures, in which the same structure is represented by the same reference sign.

DETAILED DESCRIPTION

For better understanding of this disclosure, various embodiments in the figures are described below.

Blood oxygen saturation detection has been widely used in clinical practice. Pulse oximetry waveform (e.g., amplitude and area under the curve) obtained in such detection may be related to hemodynamic effects such as cardiac output, volume condition and peripheral tissue perfusion. It is further discovered that the pulse oximetry waveform can reflect both cardio-pulmonary quality and ROSC characteristics in a CPR process. Therefore, some relevant parameters of the pulse oximetry waveform can be established in this disclosure by using the blood oxygen saturation detection method (e.g., near-infrared light detection), which means that a continuous and non-invasive method for automatic recognition of ROSC in the CPR process can be established.

Determination of blood oxygen saturation may include two parts, namely spectrophotometric determination and blood plethysmography. The spectrophotometric determination can be performed by using red light with a wavelength of about 660 nm and infrared light with a wavelength of about 940 nm. Oxyhemoglobin ($HbO_2$) has less absorption for 660 nm red light and more absorption for 940 nm infrared light, while hemoglobin (Hb) has more absorption for 660 nm red light and less absorption for 940 nm infrared light. A ratio between the infrared light absorption intensity and the red light absorption intensity can be calculated so as to determine an oxygenation degree of hemoglobin, namely the blood oxygen saturation ($SaO_2$).

Figure 1:
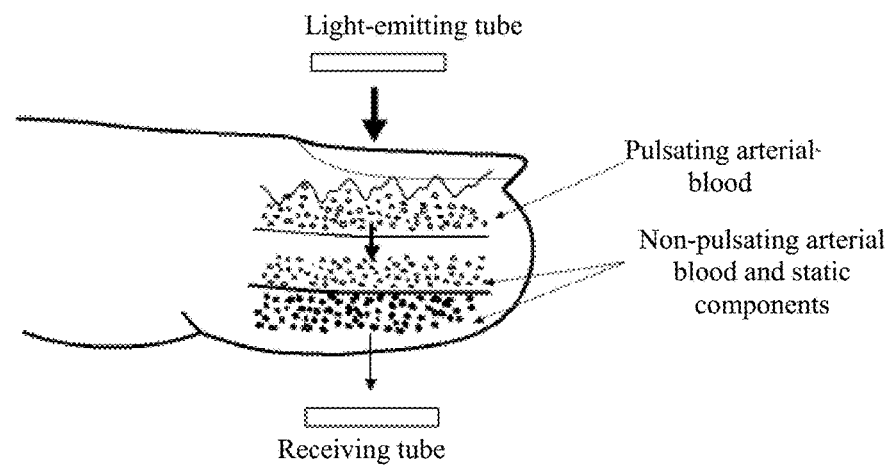
FIG. 1 is a schematic diagram for blood oxygen saturation detection.

FIG. 1 is a schematic diagram for blood oxygen saturation detection. Two light emitting tubes that emit red light and infrared light respectively can be mounted on one side of a probe, while a photoelectric detector (i.e., receiving tube) can be mounted on the other side of the probe, where the photoelectric detector may convert detected red light and infrared light that penetrate through finger arteries into electric signals. Skin, muscle, fat, venous blood, pigment and bone may have constant absorption coefficients for these two lights. Concentrations of $HbO_2$ and Hb in arterial blood may have periodic changes with arteriopalmus, thereby causing periodic changes of signal intensity outputted by the photoelectric detector. Blood oxygen saturation and pulse rate can then be determined by processing these signals having periodic changes.

When determining pulse oximetry saturation, blood perfusion should be provided. When a light beam transilluminates a peripheral tissue, the extent of attenuation of transilluminated light energy may be related to a cardiac cycle. At the time of systole, peripheral blood volume is highest, and light absorption intensity reaches a maximum value, while detected light energy reaches a minimum value. The situation is reversed at the time of diastole. Variations of light absorption intensity can reflect variations of blood volume. Varying the blood volume can change the intensity of the transilluminated light energy.

When detecting the light intensity by the photoelectric detector, a smaller value is obtained at the moment of cardiac impulse while a larger value is obtained at the cardiac impulse interval. There may be a D-value between these two values, which can be the light absorption intensity of pulsating arterial blood. In this way, a light absorption rate (R) between two wavelengths, which may be in negative correlation with $SaO_2$, can be calculated as follows: R=(AC660/DC660)/(AC940/DC940). Blood oxygen saturation of a patient can then be calculated according to a standard curve established by data of normal volunteers. A formula for calculating oxygen saturation is shown below: oxygen saturation %=oxyhemoglobin/(oxyhemoglobin+deoxyhemoglobin)*100%.

Figure 2:
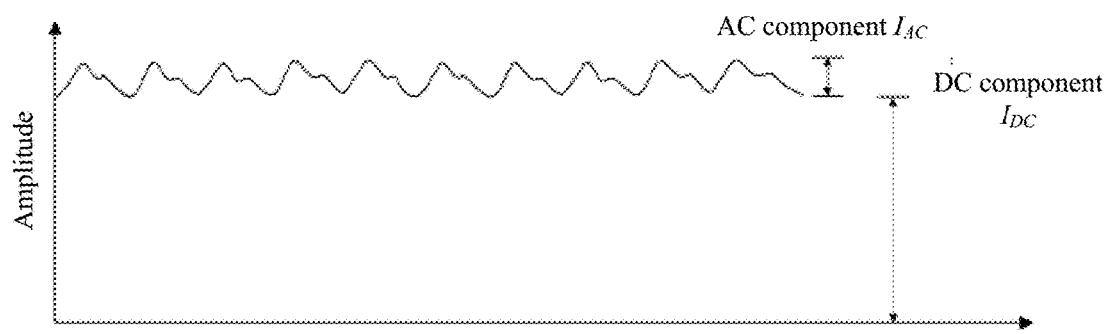
FIG. 2 is a schematic diagram for signals detected by a blood oxygen saturation sensor.

In an $SaO_2$ sensor, two light emitting diodes (LED) that emit about 660 nm red light and about 940 nm infrared light respectively may be mounted on one side, while one photoelectric detector may be mounted on an opposite side. Therefore, LEDs should be opened and closed alternatively so that the photoelectric detector can distinguish the absorption intensity under different wavelengths. Influences of ambient light on detection should be eliminated from the transilluminated light at each wavelength. When the 660 nm/940 nm light penetrates the biological tissue, there may be a difference between $HbO_2$ and Hb in light absorption intensity. Absorption at each wavelength can be a function of skin color, skin structure, iliacus muscle, blood and other tissues penetrated by the light. The light absorption intensity can be considered as a sum of pulsating absorption and non-pulsating absorption. FIG. 2 is a schematic diagram for signals detected by the $SaO_2$ sensor, in which the AC component can be caused by pulsating arterial blood, while the DC component can be caused by the light absorption intensities of non-pulsating arterial blood, venous blood and tissues. Perfusion index PI is a percentage of AC in DC (PI=AC/DC×100%). It can be seen in FIG. 2 that both the AC component and the DC component are included in the receiving information. The AC component may be related to a pulsating blood volume. In the case of weakest blood flow, the light absorption intensity of the blood may be smallest, while the transilluminated signal may be strongest, and thus the AC signal can reach a maximum value. On the other hand, the light absorption intensity of the blood may become largest, while the transilluminated signal may be weakest, and thus the AC signal may reach a minimum value. The DC component is caused by non-pulsating transilluminated intensity of muscle and bone, and it represents a minimum signal value.

In an example $SaO_2$ sampling system, e.g., in Mindray™'s blood oxygen system, a voltage range of a sampled signal can be about 0-5 V, and its mapped sampled data can have a range of about 0-2,097,152 V. As a result, a calculated least significant bit (LSB) value can be about 2.38, namely each sampled value may correspond to $2.38^{\mu V}$. In this disclosure, various features of respective blood oxygen parameters can be described according to voltage characteristic.

Figure 5:
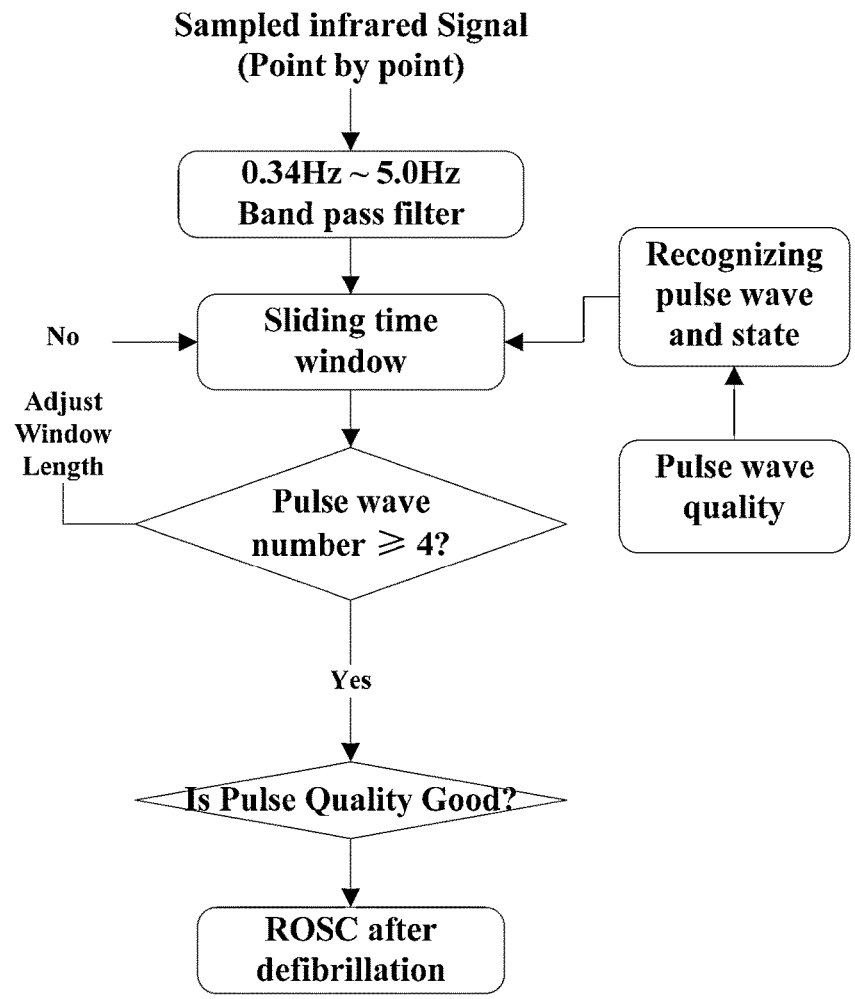
FIG. 5 is a flow chart for an ROSC recognition method after defibrillation.

Basic hemodynamic features may disappear with a cardiac arrest, in which case the sampled signal may look like a noise line. When there is ROSC, the sampled signal can have corresponding regular pulse features. Therefore, whether there is ROSC after defibrillation can be recognized based on a change from noise line to regular pulse feature. Pulse feature recognition based on a sampled signal can be non-invasive, convenient, high in response speed and adaptive for the urgent CPR process. In this disclosure, a method for recognizing ROSC after defibrillation is provided on the basis of sampling red/infrared light signals. Since the infrared light is less interfered with when compared with the red light, this disclosure describes the above-mentioned ROSC recognition method after defibrillation using the sampled infrared light signals as an example (FIG. 5).

In order to eliminate noise interference beyond physiological band, the infrared light signals can first be filtered in real time by using a band pass filter of about 0.34-5.0 Hz. A sliding time window can be established to find out whether the pulse features appear therein. ROSC after defibrillation can be determined when there are respectively noise lines and regular pulses wave at the front and back ends of the time window, the pulse wave number reaches about 4-6, and a single pulse wave has relatively good quality. According to current guidelines for CPR, an interruption period between compressions should not exceed about 10 seconds. Therefore, such recognition can be performed precisely when there are at least about six pulse waves within about 10 seconds. A spontaneous cardiac rhythm more than about 36 times per minute can thus be accurately recognized by the method of this disclosure, where the spontaneous cardiac rhythm (time per minute) can be obtained by multiplying a frequency of spontaneous cardiac rhythm by 60. In this embodiment, the pulse wave number used as a determination criterion can be adaptively set according to system features, and a time duration of the sliding time window can be adaptively adjusted according to the frequency of the pulse wave. Quality of the single pulse wave can be determined by its amplitude, width and shape. An amplitude inspection may refer to amplitude consistency (e.g., with fluctuation of less than about 10%) between a current pulse wave and at least about three historical pulse waves. When those pulse waves have no consistency in amplitude, the amplitude quality may be deemed to be poor. A width inspection may refer to width consistency (e.g., with fluctuation of less than about 10%) between the time lengths (i.e., cardiac rhythm) of the current pulse wave and the at least about three historical pulse waves. When those pulse waves have no consistency in width, the width quality may be deemed to be poor. A shape inspection may refer to a shape correlation between the shapes of the current pulse wave and the at least about three historical pulse waves. When the correlation is less than about 80%, the shape quality may be deemed to be poor. By considering amplitude, width and shape, the quality level of the single pulse wave can be obtained for further evaluation. In this embodiment, the thresholds can be adaptively adjusted according to system features. The recognition of a pulse wave within the sliding time window can be performed by any suitable recognition method such as a difference method and an inflection point method.

Figure 3:
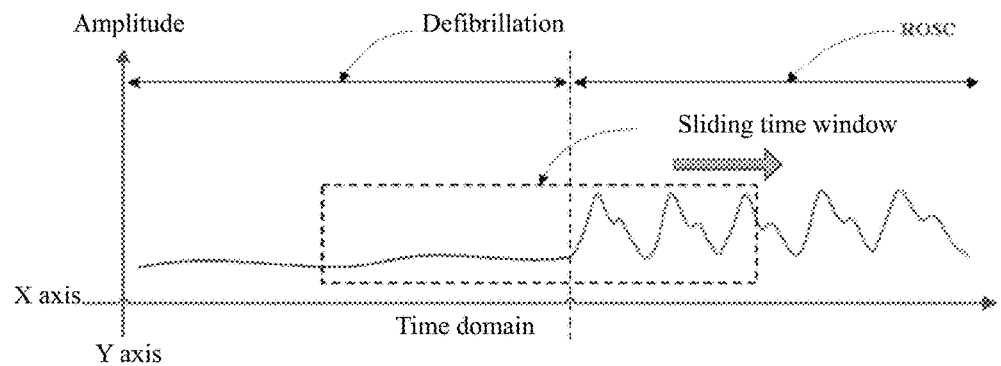
FIGS. 3 and 4 show two change modes of physiological characteristics of cardiac motion in a CPR process.
Figure 4:
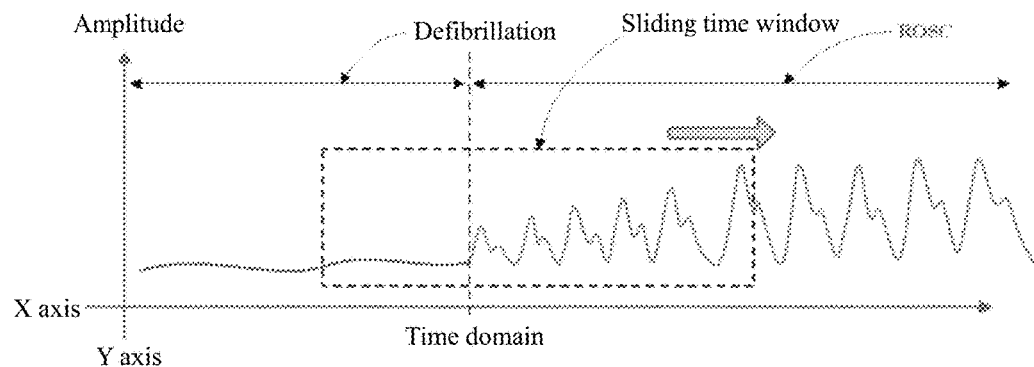

Based on the physiological features of cardiac motion in the CPR process, there may be two change modes for cardiac impulse. On one hand, the cardiac impulse may suddenly appear and become stable immediately. On the other hand, the pulses may grow stronger gradually and become stable finally. FIGS. 3 and 4 respectively show these two change modes.

In FIG. 3, the "defibrillation" period shows that the sampled signals have no physiological features of the pulse wave. The "ROSC" period shows that the patient has restored his/her spontaneous circulation with stable and regular pulse waves after a successful defibrillation.

In FIG. 4, the "defibrillation" period shows that the sampled signals have no physiological features of the pulse wave. The "ROSC" period shows that the patient has restored his/her spontaneous circulation after a successful defibrillation, where the regular pulse waves grow stronger and gradually become stable.

When performing external compressions in the presence of spontaneous circulation, filling and ejection functions of a normal heart may be interfered due to non-synchronization between rhythm and time phase of manual compression and cardiac systolic and diastolic functions under the spontaneous circulation, which may influence normal cardiac pump function and cause reduction in stroke volume. In an initial stage of ROSC, the patient's heart rate may have gradual changes from slow to fast due to vasoactive drugs used in a rescue process, and stimulation from the external compression and physiological compensation mechanism. However, there may not be spontaneous cardiac rhythm with gradual changes in patients having serious heart failure, abnormal conduction, or abnormal cardiac electrical activity. This may be related to the pathological loss of the compensation mechanism. These patients may have slow or fast arrhythmia, i.e., their cardiac rates are less than about 60 times (beats) per minute or more than about 120 times per minute, which can be distinguished from external compression frequency.

When the patient has restored his/her spontaneous circulation in the CPR process, the manual compression may disturb the normal spontaneous circulation, and the spontaneous cardiac rhythm can have gradual changes if the patient has relatively good cardiac function. On the other hand, the spontaneous cardiac rhythm may be maintained at a rate of less than about 60 times per minute or more than about 120 times per minute if the patient has relatively poor cardiac function. All these can provide advantageous physiological features for the ROSC recognition in the CPR process of this disclosure.

Two kinds of signals can be found when analyzing the features of ROSC in the CPR process. That is, the manual compression can form one waveform signal, while the spontaneous circulation can form another waveform signal. Those signals formed by the manual compression and the spontaneous circulation (i.e., manual compression signal and spontaneous circulation signal) may be superposed and mixed to form a special waveform showing there is ROSC in the CPR process.

Figure 6:
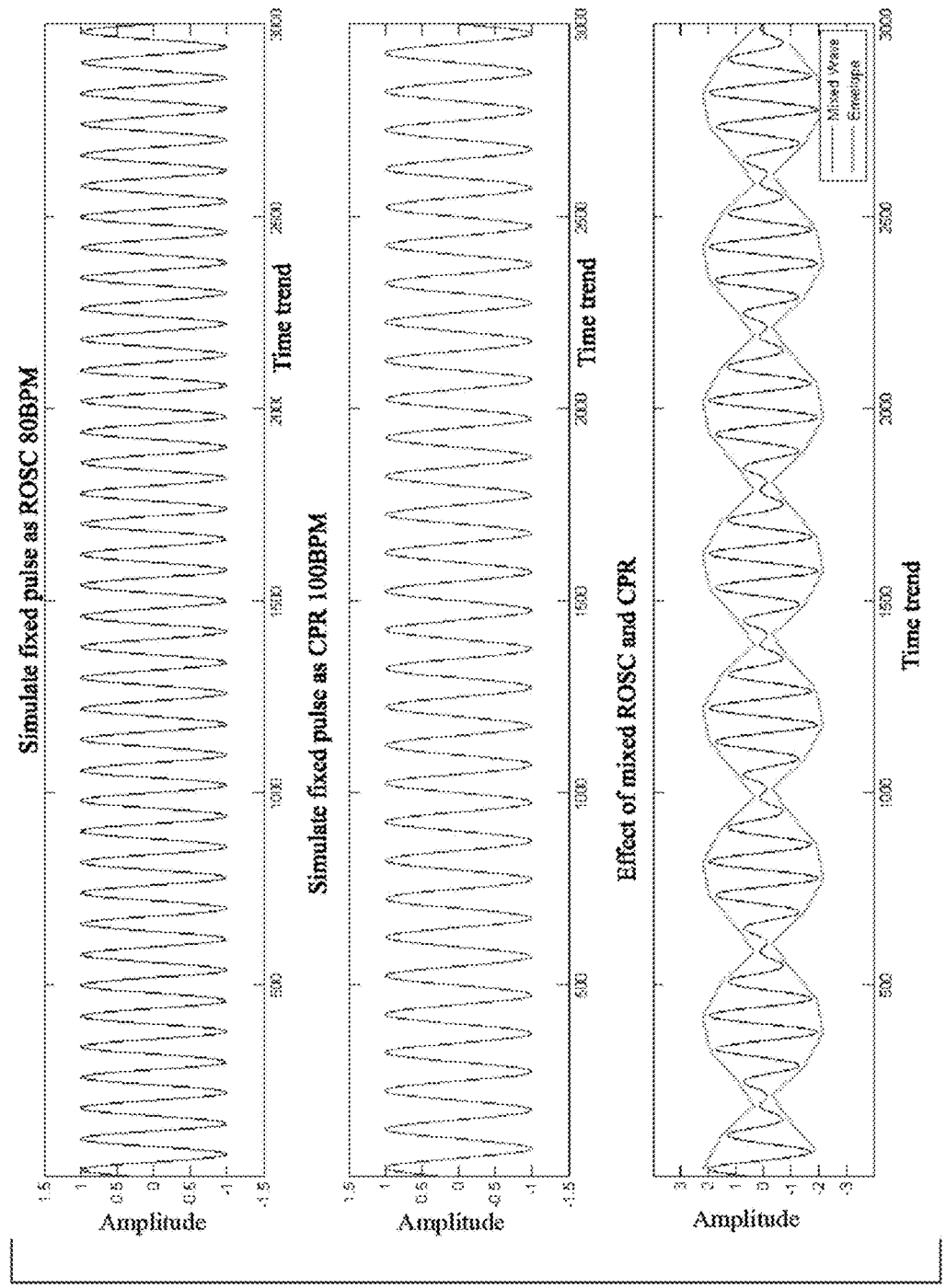
FIG. 6 is a schematic diagram for a mixed waveform of manual compression signals and spontaneous circulation signals.
Figure 7A:
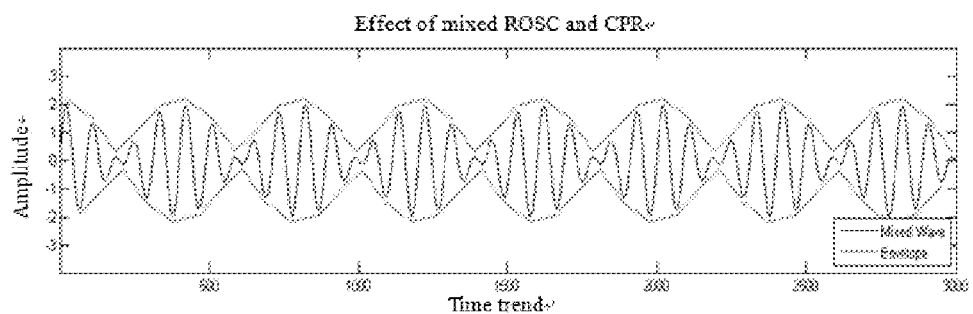
FIGS. 7A-7D are schematic diagrams for mixed waveforms of manual compression signals and spontaneous circulation signals with a phase deviation of 0°, 90°, 180° and 270° respectively.
Figure 7B:
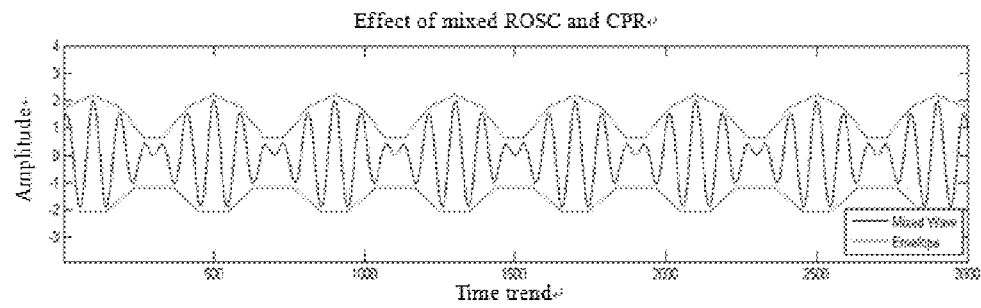
Figure 7C:
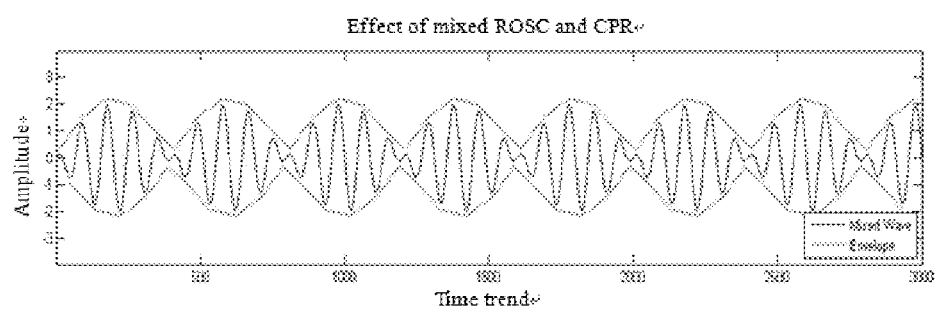
Figure 7D:
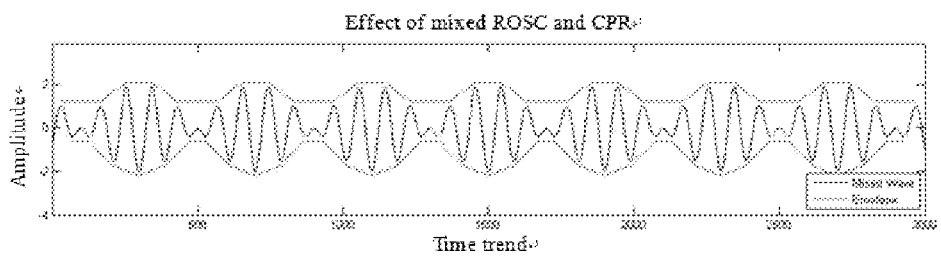

The manual compression signal may be formed by stable compression with a fixed frequency and fixed depth, such as a sine wave of about 100 BPM. The spontaneous circulation signal may have a fixed frequency, such as a sine wave of about 80 BPM. As shown in FIG. 6, the mixed waveform of the manual compression signal and the spontaneous circulation signal may have a regular envelope. As described by the envelope line and the area showing the "effect of mixed ROSC and CPR," the regular envelope characteristic can be identified, which cannot be shown by any single-way signal. This envelope characteristic thus can provide an effective feature point for the ROSC recognition in the CPR process.

In practical application, there should be phase deviation between the manual compression signal and the spontaneous circulation signal, i.e., these two signals are not in 0° phase alignment with each other. As shown in FIGS. 7A-7D, there may be phase deviations of 0°, 90°, 180° and 270° between the manual compression signal and the spontaneous circulation signal, which can indicate the envelope specificity of the mixed waveform. Based on some theoretical analysis, those fixed phase deviations may have no apparent influence on the envelope characteristic of the mixed signal. That is, the phase difference may not affect the regularity of an envelope rhythm.

Figure 8:
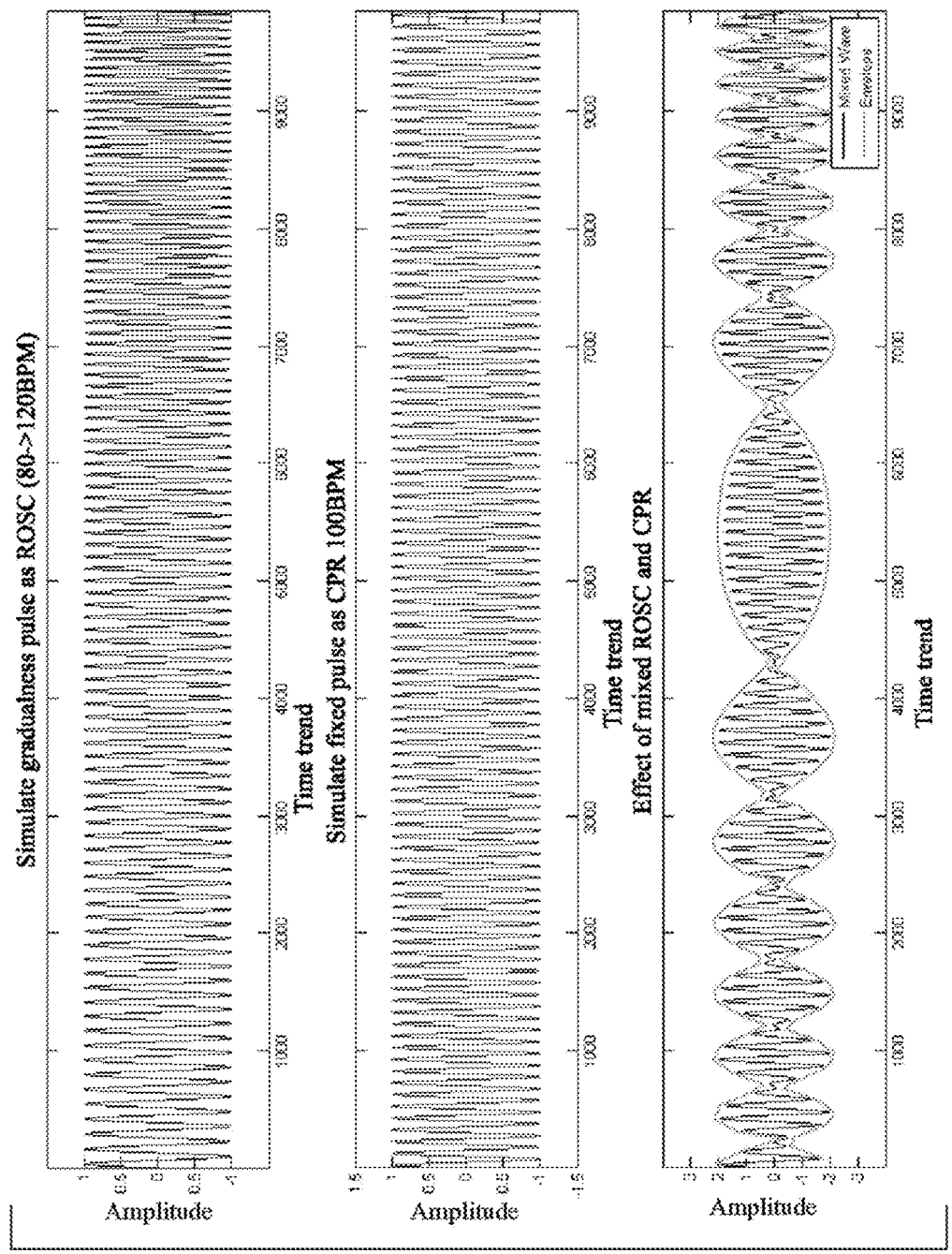
FIG. 8 is a schematic diagram for a mixed waveform of manual compression signals and spontaneous circulation signals when spontaneous cardiac rhythm has gradual changes in the process of external compression.
Figure 9A:
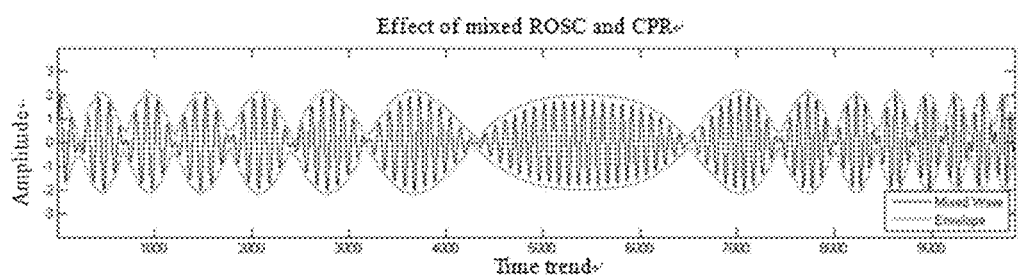
FIGS. 9A-9D are schematic diagrams for mixed waveforms of manual compression signals and spontaneous circulation signals with a phase deviation of 0°, 90°, 180° and 270° respectively when spontaneous cardiac rhythm has gradual changes in the process of external compression.
Figure 9B:
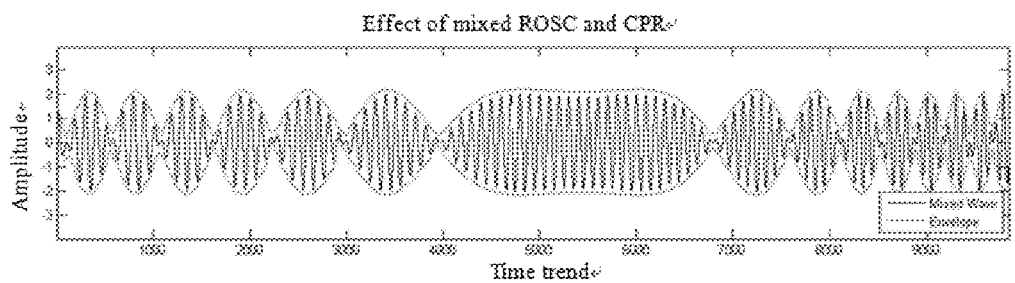
Figure 9C:
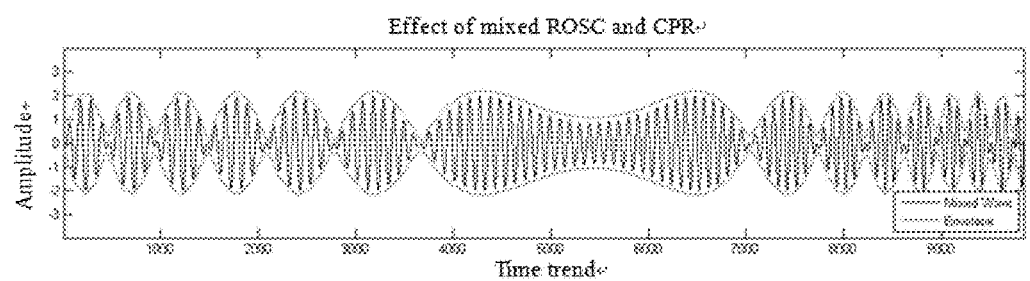
Figure 9D:
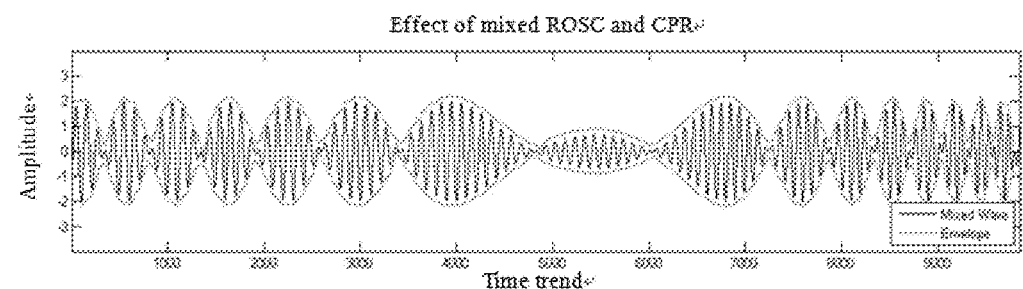

As described by such physiological features, the spontaneous cardiac rhythm can have gradual changes during external compression. Based on this point, a mode can be deduced in this disclosure, where the manual compression signal can be a sine wave of fixed 100 BPM, and the spontaneous cardiac rhythm signal can be a sine wave with gradual change from about 80 BPM to about 120 BPM. The mixed waveform of these two signals is shown in FIG. 8.

According to the deduced mode, the mixed waveform may still have a regular envelope rhythm characteristic when the spontaneous cardiac rhythm increases gradually. An envelope shape may depend on the spontaneous cardiac rhythm and the compression frequency. The larger the frequency deviation, the narrower the envelope width. The smaller the frequency deviation, the wider the envelope width. Herein, the widest envelope in FIG. 8 corresponds to the situation where the spontaneous cardiac rhythm and the compression frequency are the same.

As shown in FIGS. 9A-9D, the phase deviation between the spontaneous cardiac rhythm and the compression frequency may have no influence on the envelope rhythm characteristic.

As described above, with the occurrence of ROSC, the physiological signals can often have the envelope characteristic during external compression. Therefore, it can be deemed that the patient has restored his/her spontaneous circulation when some continuous and regular envelope characteristics are recognized. The following exemplary feature recognition logic can be established based on such features.

Peak points of each pulse wave of the physiological signals can be recognized by any suitable methods such as a difference transformation method and a slope transformation method. Missing parts between the peak points of the pulse waves can then be compensated by linear interpolation or curve fitting to maintain time synchronization with some original sampled signals and form a positive envelope curve (PE curve).

Time information $$\sum_{n=0}^{N-1} PE_{Time}(n)$$

and amplitude information $$\sum_{n=0}^{N-1} PE_{Amp}(n)$$

of the peak points of the PE curve can be recognized and recorded by any suitable methods such as a difference transformation method and a slope transformation method.

Valley points of each pulse wave of the physiological signals can be recognized by any suitable methods such as a difference transformation method and a slope transformation method. Missing parts between the valley points of the pulse waves can then be compensated by linear interpolation or curve fitting to maintain time synchronization with some original sampled signals and form a negative envelope curve (NE curve).

Time information $$\sum_{n=0}^{N-1} NE_{Time}(n)$$

and amplitude information $$\sum_{n=0}^{N-1} NE_{Amp}(n)$$

of the valley points of the NE curve can be recognized and recorded by any suitable methods such as a difference transformation method and a slope transformation method.

Width information of each envelope can be recognized and recorded. Variations of amplitude $$\sum_{n=j}^{N-1} PNE_{Amp}(n)$$

(i.e., envelope amplitude PNE) of corresponding time points on PE and NE can be evaluated by any suitable methods such as a difference transformation method and a slope transformation method. After that, the time information $$\sum_{n=0}^{N-1} PNE_{Time}^{Max}(n)$$

corresponding to a maximum $$\sum_{n=0}^{N-1} PNE_{Amp}^{Max}(n)$$

of the envelope amplitude PNE or the time information $$\sum_{n=0}^{N-1} PNE_{Time}^{Min}(n)$$

corresponding to a minimum $$\sum_{n=0}^{N-1} PNE_{Time}^{Min}(n)$$

of the envelope amplitude PNE can be found. A time width $$\sum_{n=0}^{N-2} PNE_{trueWidth}(n)$$

of the envelope can be obtained when calculating a D-value between the times at an Nth maximum and an N−1th maximum or at an Nth minimum and an N−1th minimum. Some related formulas are shown as below.

$$\sum_{n=0}^{N-1} PNE_{Amp}(n) = \sum_{n=0}^{N-1} PE_{Amp}(n) - \sum_{n=0}^{N-1} NE_{Amp}(n)$$

$$\sum_{n=0}^{N-2} PNE_{tmWidth}(n) = \sum_{n=1}^{N-1} [PNE_{Time}^{Max}(n) - PNE_{Time}^{Max}(n-1)]$$

$$\sum_{n=0}^{N-2} PNE_{tmWidth}(n) = \sum_{n=1}^{N-1} [PNE_{Time}^{Min}(n) - PNE_{Time}^{Min}(n-1)]$$

Time points $$\sum_{n=0}^{N-1} PE_{Time}^{Max}(n)$$

and $$\sum_{n=0}^{N-1} NE_{Time}^{Min}(n)$$

that correspond to each envelope maximum $$\sum_{n=0}^{N-1} PE_{Amp}^{Max}(n)$$

of the PE amplitude and to each envelope minimum $$\sum_{n=0}^{N-1} NE_{Amp}^{Min}(n)$$

of the NE amplitude can be first determined. After that, an envelope time deviation factor $$\sum_{n=0}^{N-1} PNE_{tmBias}(n)$$

can be established by the determined time points. Its calculation formula is shown below:

$$\sum_{n=0}^{N-1} PNE_{tmBias}(n) = \sum_{n=1}^{N-1} [PE_{Time}^{Max}(n) - NE_{Time}^{Min}(n)]$$

Based on the above-described recognition logic, the following characteristic values can be established: maximum $$\sum_{n=0}^{N-1} PNE_{Amp}^{Max}(n)$$

and minimum $$\sum_{n=0}^{N-1} PNE_{Amp}^{Min}(n)$$

information of envelope amplitude, envelope width information $$\sum_{n=0}^{N-2} PNE_{tmWidth}(n),$$

and envelope time deviation factor $$\sum_{n=0}^{N-1} PNE_{tmBias}(n).$$

Figure 10:
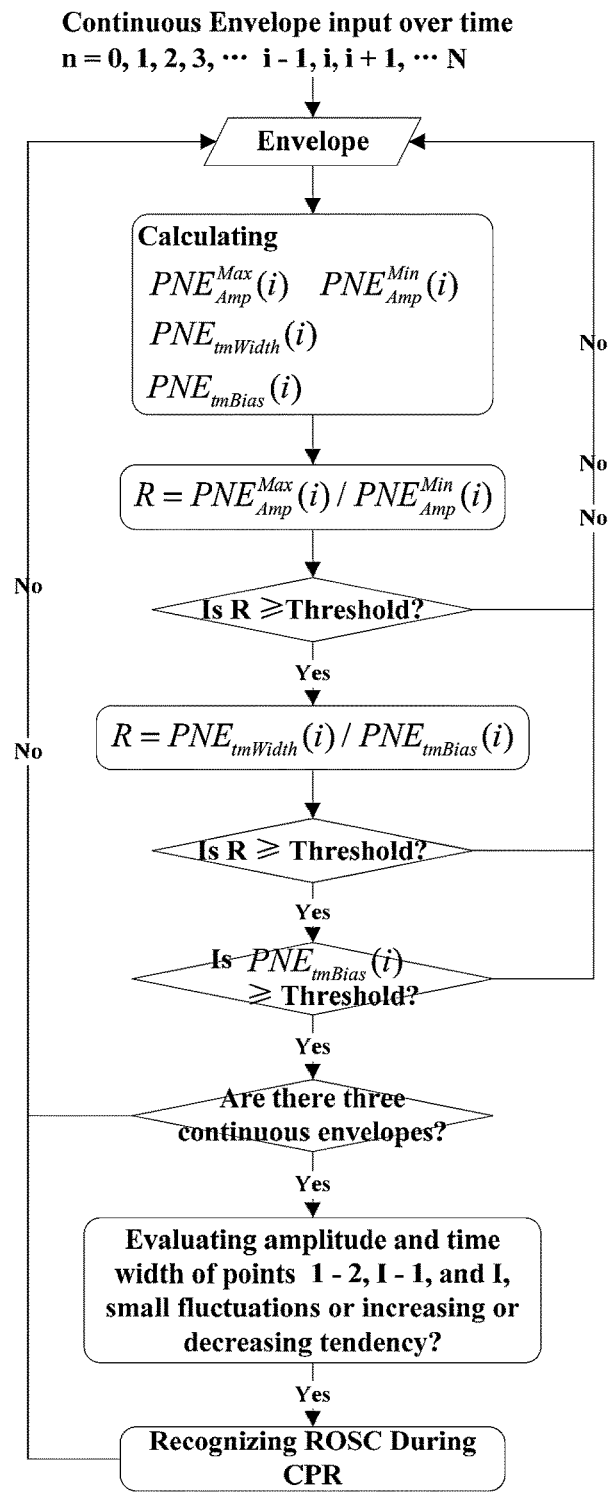
FIG. 10 is a flow chart for an exemplary time-domain ROSC recognition logic.

Whether there is a regular envelope feature can be evaluated by these established characteristic values. The maximum $$\sum_{n=0}^{N-1} PNE_{Amp}^{Max}(n)$$

and minimum $$\sum_{n=0}^{N-1} PNE_{Amp}^{Min}(n)$$

information of the envelope amplitude may correspond to an amplitude ratio that should meet a certain value. The envelope width information $$\sum_{n=0}^{N-2} PNE_{tmWidth}(n)$$

and the envelope time deviation factor $$\sum_{n=0}^{N-1} PNE_{tmBias}(n)$$

should also meet a certain ratio, and the envelope time deviation factor $$\sum_{n=0}^{N-1} PNE_{tmBias}(n)$$

should be smaller than a certain time length. After meeting the criteria above, whether there are at least about three continuous envelopes can be evaluated. ROSC can be determined when at least about three continuous envelopes can be detected, and the amplitude $$\sum_{n=0}^{N-1} PNE_{Amp}^{Max}(n)$$

as well as the width $$\sum_{n=0}^{N-1} PNE_{Amp}^{Min}(n)$$

have small fluctuations or meet a certain increasing or decreasing tendency feature. Otherwise, there is no spontaneous cardiac rhythm. FIG. 10 shows a flow chart for such exemplary time-domain recognition logic.

Figure 11:
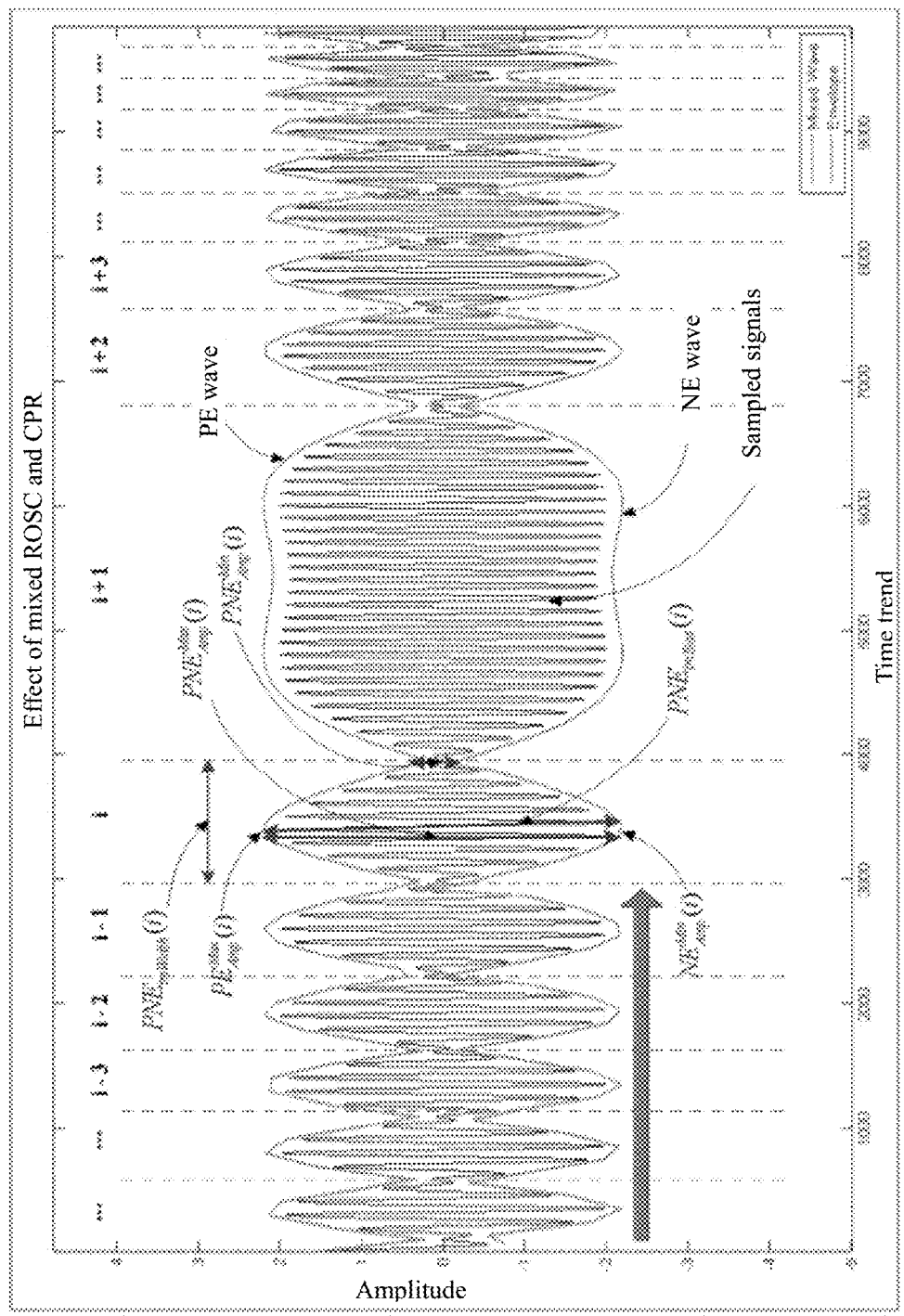
FIG. 11 shows some calculation parameters in a time-domain ROSC recognition logic on a waveform.

Due to the differences between the compression frequency and the spontaneous circulation frequency, the formed envelope may include different numbers of pulse peaks. When evaluating according to the envelope, the evaluation time may be inconsistent. Generally speaking, ROSC can be determined and recognized within about 30 seconds. Herein, FIG. 11 shows some calculation parameters on a waveform.

Figure 12:
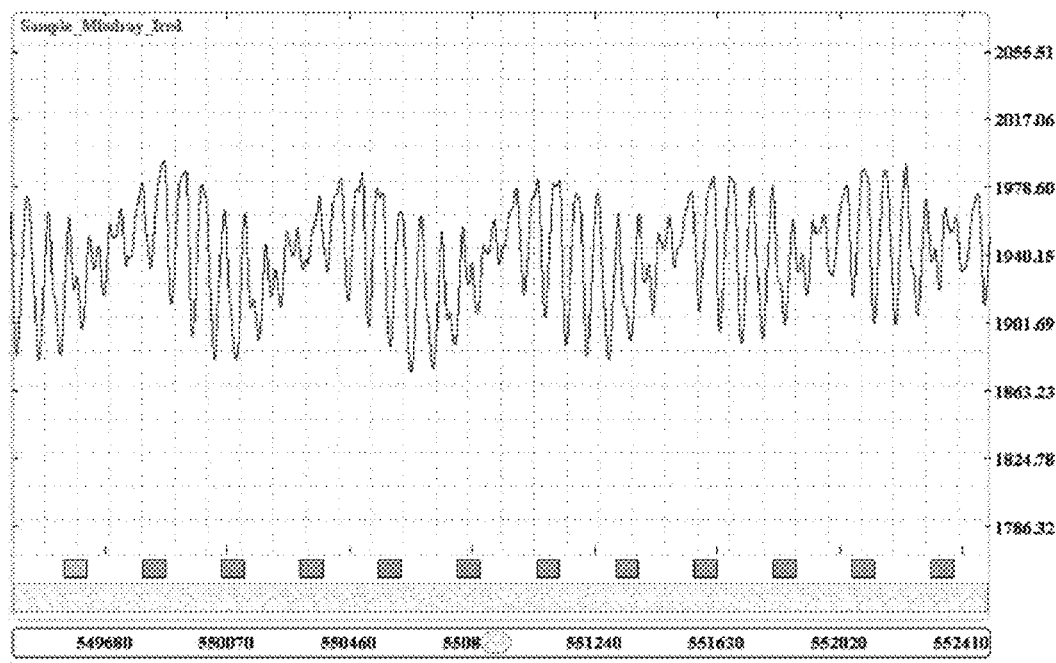
FIG. 12 shows an exemplary waveform generated when applying a time-domain ROSC recognition logic to an animal experiment.

As shown in FIG. 12, such regular envelope has been found in animal experiments. The above-described time-domain feature recognition logic can precisely find and recognize ROSC in the CPR process while further providing some prompt information.

Figure 13:
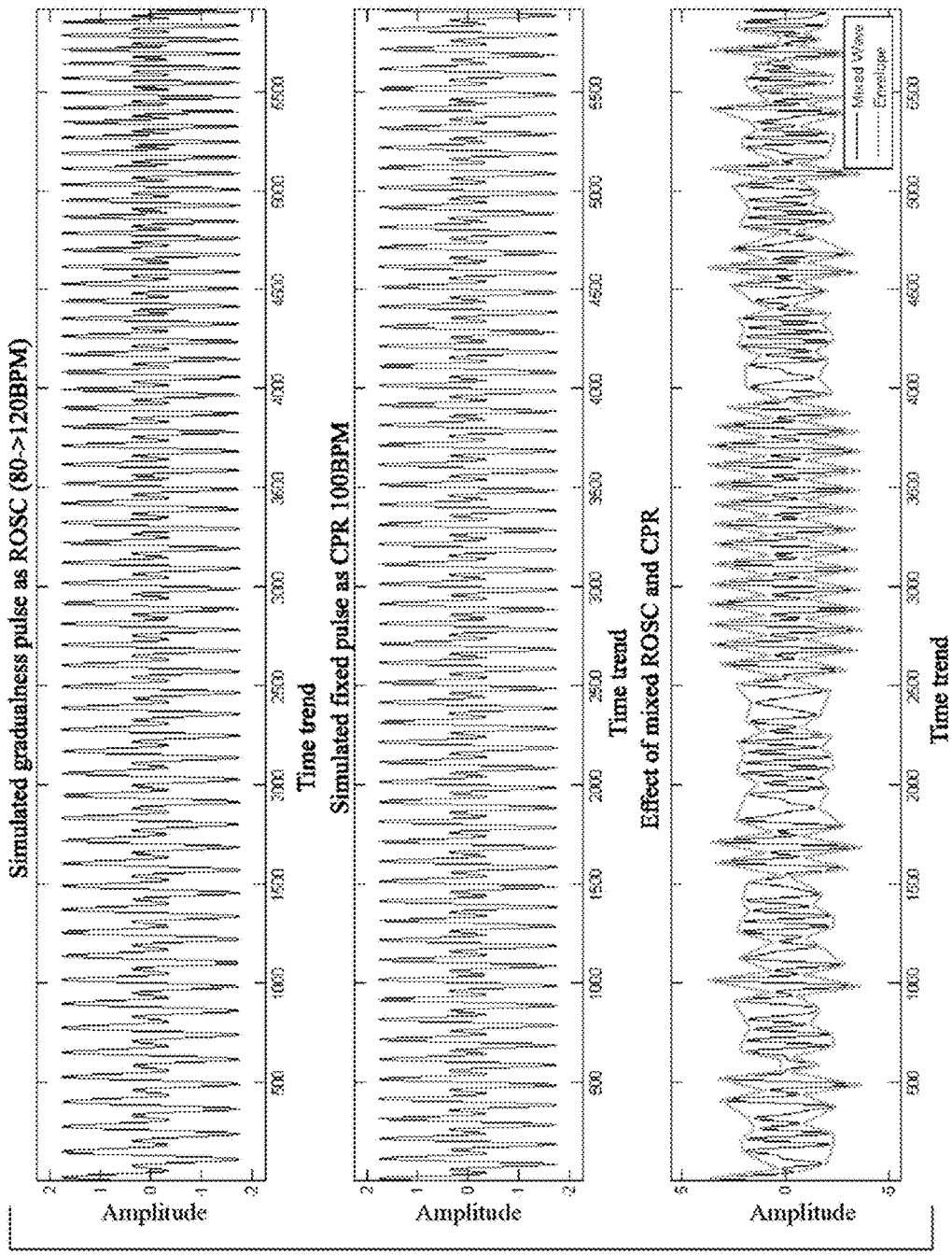
FIG. 13 is a schematic diagram for a mixed waveform of manual compression signals and spontaneous circulation signals when there is interference on these signals.

Time-domain feature recognition is well-known to present dynamic signals on a time axis, thereby having the advantages of accuracy and intuition, and having a relatively high correlation with the shape of the pulse wave. When there is motion interference, baseline drift and patient cardiac dysfunction, the waveform in time domain may have disorder, in which case the recognition based on the envelope feature may be affected. As shown in FIG. 13, the pulse wave has some physiological echo (which is caused by ejection rebound of a blood vessel), and the envelope feature thus shows certain interfered characteristics. Through particular mathematic rules, the frequency domain method can convert the signals into a figure with a frequency axis as the coordinate. In this case, the signals with different frequencies can be reflected at different locations on the frequency axis directly. It can be seen that the frequency domain method may have some advantages when compared with the time domain method. As a result, this disclosure further describes the feature recognition of ROSC in the CPR process in terms of frequency-domain feature recognition.

Figure 14:
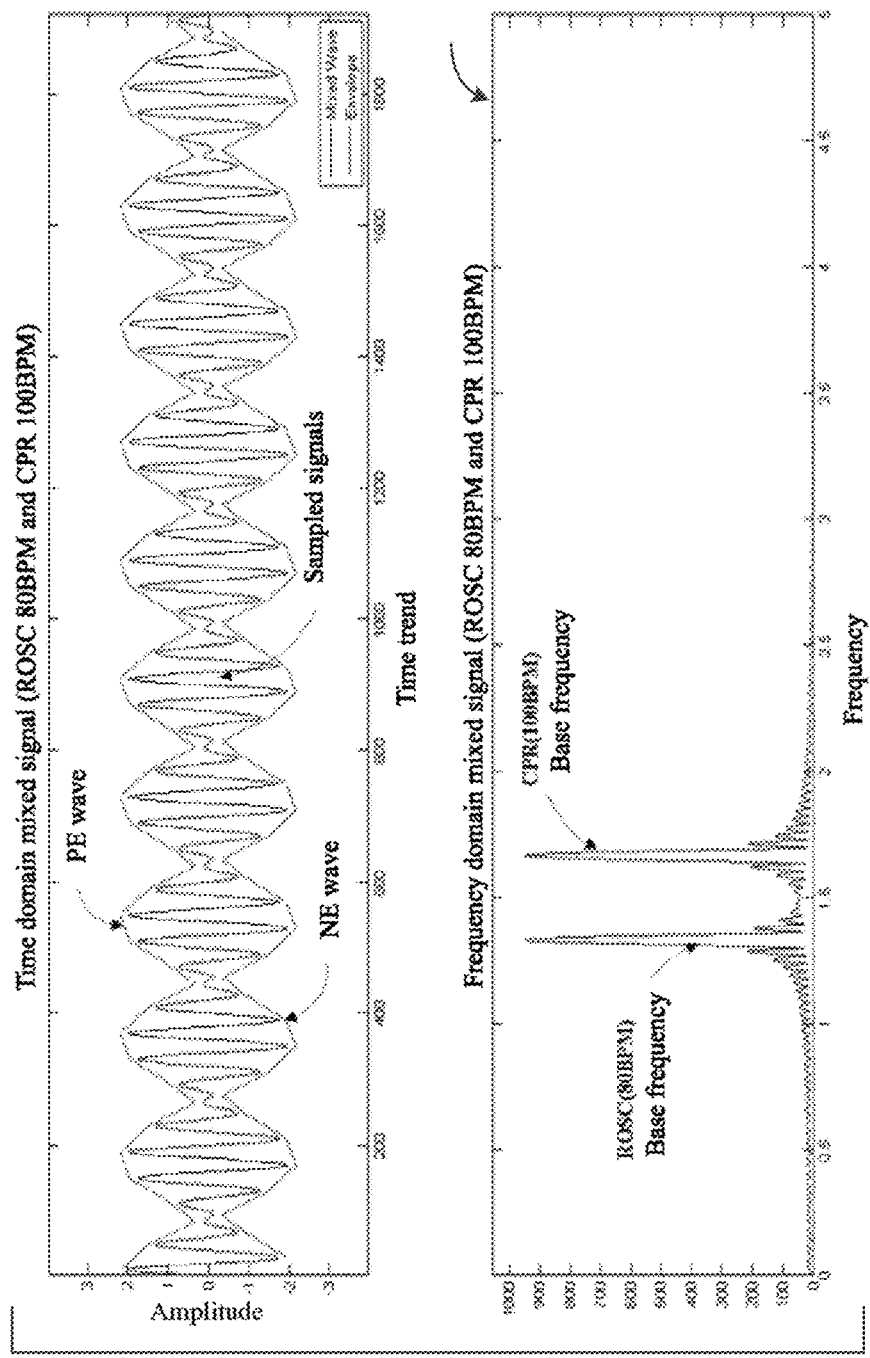
FIG. 14 is a schematic diagram for a mixed waveform and a spectral distribution of manual compression signals and spontaneous circulation signals when manual compression frequency and spontaneous cardiac rhythm are inconsistent with each other.

Phase deviation of a time-domain waveform can be eliminated in the frequency domain due to frequency-domain characteristics. If the spontaneous cardiac rhythm and the external compression frequency are different, two independent spectral peaks can be formed in the frequency spectrum. Assuming that the spontaneous cardiac rhythm is a sine wave of about 80 BPM and the external compression frequency is a sine wave of about 100 BPM, their mixed waveform and spectral distribution can be shown as FIG. 14. Theoretically, two spectral peaks at different frequencies would be present in the frequency spectrum when the spontaneous cardiac rhythm and the external compression frequency are different. As shown in FIG. 14, the spontaneous cardiac rhythm can form a spectral peak at about 1.33 Hz, while the external compression can form a spectral peak at about 1.67 Hz.

Figure 15:
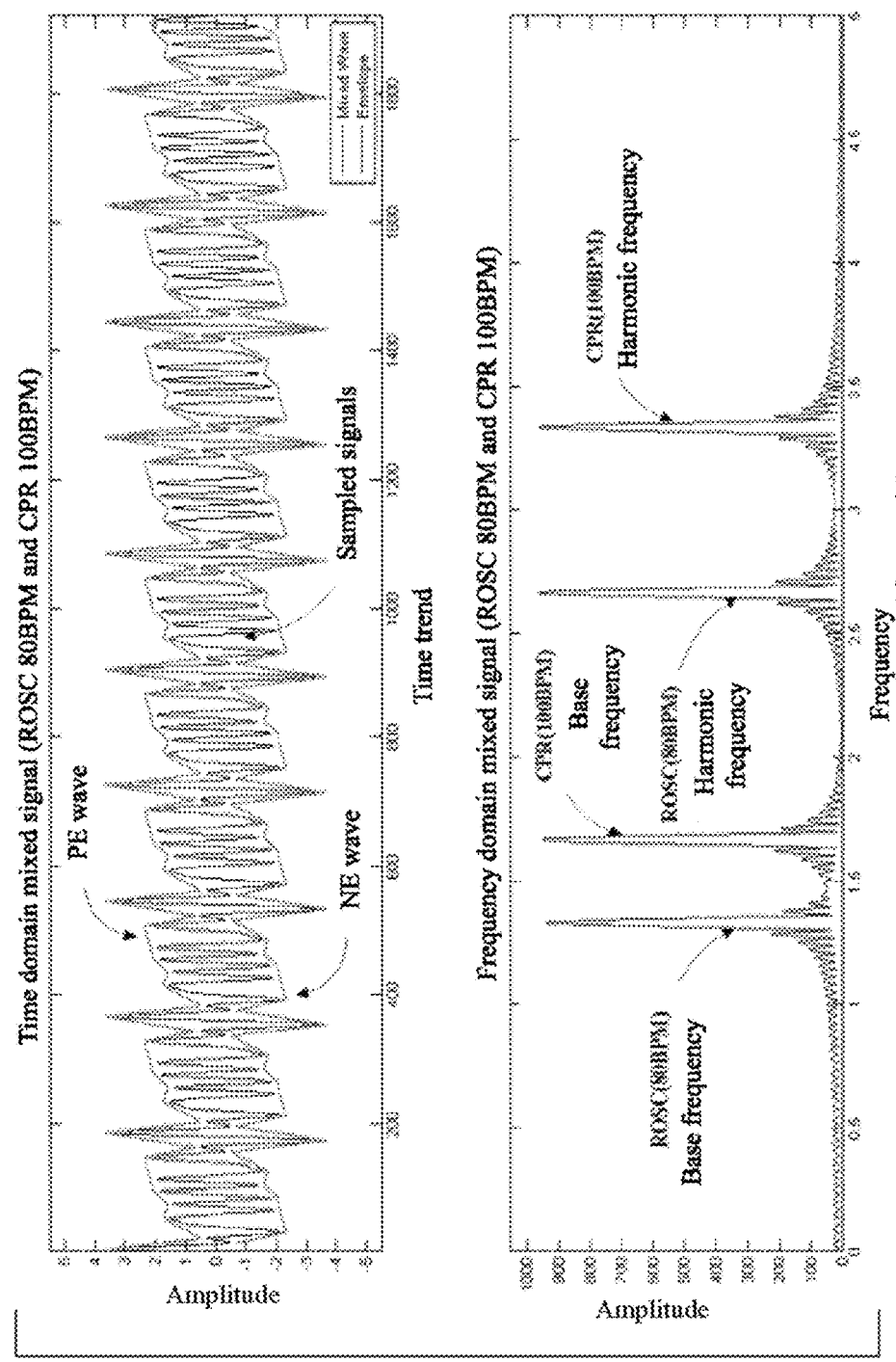
FIG. 15 is a schematic diagram for a mixed waveform and a spectral distribution of manual compression signals and spontaneous circulation signals when manual compression frequency and spontaneous cardiac rhythm are inconsistent with each other, and manual compression signals and spontaneous cardiac rhythm signals have harmonic spectral components.

The physiological signals may often include several sine waves instead of a single sine wave. In clinical applications, both the external compression signals and the spontaneous cardiac rhythm signals can have harmonic spectral components. Assuming that the spontaneous cardiac rhythm is a sine wave of about 80 BPM (having first harmonic information) and the external compression frequency is a sine wave of about 100 BPM (having first harmonic information), their mixed waveform and spectral distribution can be shown as FIG. 15. Theoretically speaking, harmonic frequency may often be n multiples of a base frequency (e.g., n=1, 2, 3 . . . N), namely an nth harmonic spectral peak can be found on the frequency axis at n multiples of the base frequency. As shown in FIG. 15, a first harmonic frequency of the spontaneous cardiac rhythm can be found at about 2.67 Hz, while a first harmonic frequency of the external compression frequency can be found at about 3.33 Hz. It can be seen that the harmonic components would neither cause interference to the base frequency information nor have mutual interference among themselves, and the spectral peaks of the external compression and the spontaneous cardiac rhythm may still be located at different frequencies.

A formula for a harmonic location is as follows:

$F_{Harmonic}(n)=F_{Basic}*(1+n)$, where $F_{Harmonic}(n)$ represents the frequency of an nth harmonic component and $F_{Basic}$ represents the base frequency.

Figure 16:
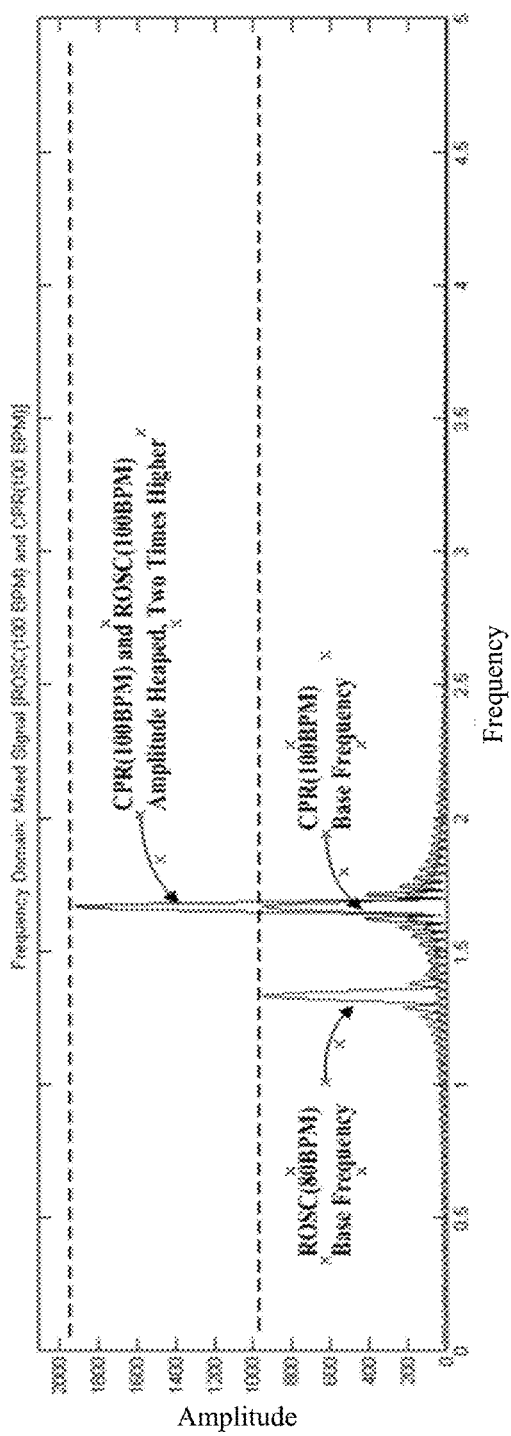
FIG. 16 is a schematic diagram for a spectral distribution of manual compression signals and spontaneous circulation signals when manual compression frequency and spontaneous cardiac rhythm are basically consistent with each other.

The descriptions above have shown the situation where the external compression frequency and the spontaneous cardiac rhythm are inconsistent. In clinical practice, those two frequencies can be basically consistent with each other. Assuming that both the spontaneous cardiac rhythm and the external compression frequency are sine waves of about 100 BPM, their spectrogram can be shown as FIG. 16. For the purpose of contrasting with a mixed spectral peak (a higher spectral peak) formed by the spontaneous cardiac rhythm and the external compression frequency of about 100 BPM, two lower spectral peaks in this figure respectively stand for the spontaneous cardiac rhythm of about 80 BPM and the external compression frequency of about 100 BPM. Amplitude of an overlapping spectral peak is a summation of the amplitudes of the respective independent spectral peaks. As shown in FIG. 16, the amplitude of the mixed spectral peak is a summation of the spectral peaks formed by the spontaneous cardiac rhythm and the external compression. It can be seen that the spectral amplitude can have significant changes in the case of the overlapping frequency.

Figure 17:
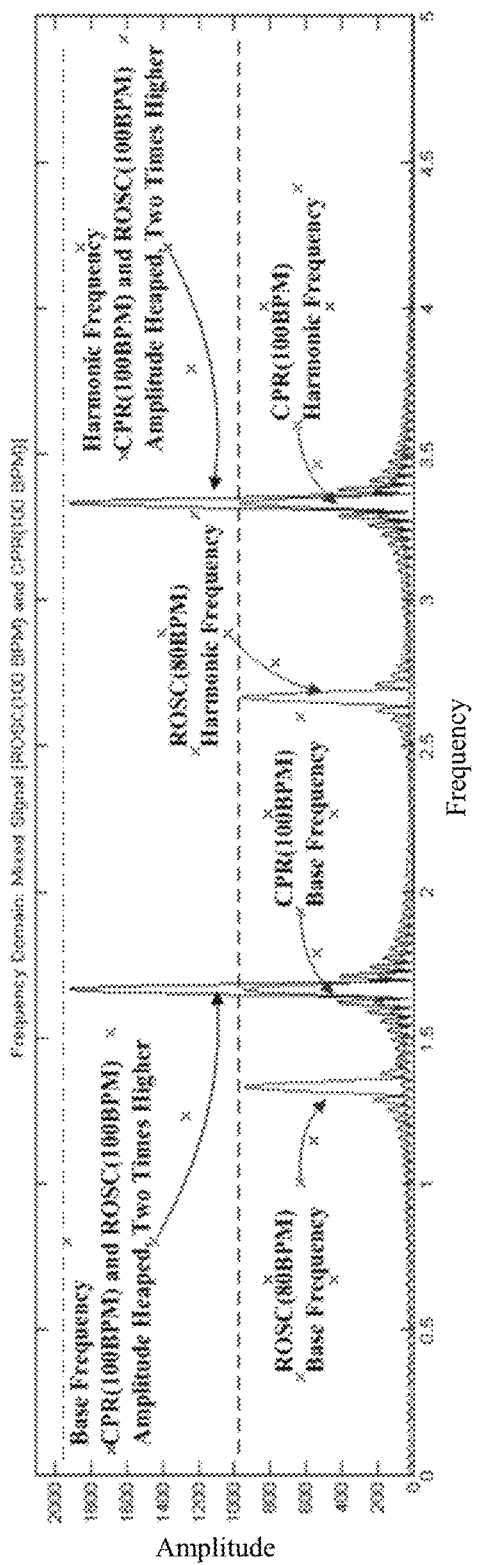
FIG. 17 is a schematic diagram for a spectral distribution of manual compression signals and spontaneous circulation signals when manual compression frequency and spontaneous cardiac rhythm are basically consistent with each other, and manual compression signals and spontaneous cardiac rhythm signals have harmonic spectral components.

The physiological signals may often include several sine waves instead of a single sine wave. Assuming that the spontaneous cardiac rhythm is a sine wave of about 100 BPM (having first harmonic information) and the external compression frequency is a sine wave of about 100 BPM (having first harmonic information), their spectral distributions can be shown as FIG. 17. Theoretically speaking, the harmonic component would have no influence on the accumulation effect of the overlapping frequencies. As shown in FIG. 17, the overlapping spectral peak at the base frequency still has an amplitude as a summation of the amplitudes at the base frequencies of the spontaneous cardiac rhythm and the external compression frequency, and the overlapping first harmonic spectral peak still has an amplitude as a summation of the amplitude of the first harmonic spectral peaks of the spontaneous cardiac rhythm and the external compression frequency. Lower spectral peaks in FIG. 17 respectively stand for the base frequency information and the harmonic frequency information of the spontaneous cardiac rhythm of about 80 BPM and the external compression frequency of about 100 BPM. Those lower spectral peaks may function as the amplitude reference so as to show the amplitude accumulation effect.

As described above, the physiological signals (detected by a pulse oximeter) may exhibit apparent spectral features with the presence of spontaneous cardiac rhythm during external compression. In the case where there are inconsistent frequencies between the spontaneous cardiac rhythm and the external compression, two spectral peaks can be formed in the frequency spectrum; in contrast, the amplitude of the spectral peak may have significant change. For these reasons, the patient may have spontaneous circulation function when there are spectral peaks at different frequencies, or when the amplitudes of certain spectral peaks have significant changes. Based on such features, an exemplary frequency-domain recognition logic can be established as below.

Sampled infrared light signals can be selected as original signals for the spectral analysis. Sampled red light signals or both kinds of signals can also be used for the analysis. In this disclosure, since the infrared light may have better anti-inference capability, the corresponding analysis will be carried out based on the infrared light. The sampled infrared light signals within a certain time duration can be selected as the data to be converted for the spectral analysis. In the case where the data segment is too long, there may be a time delay for the feedback of physiological information. In the case where the data segment is too short, the physiological information may be insufficient. Such time duration can be adaptively adjusted according to the requirements of system analysis. In combination with practical applications, the data within about four to six seconds may be chosen to be converted for the spectral analysis.

The time-domain data within about four to six seconds may be converted into corresponding frequency-domain data. Fast Fourier Transformation (FFT) or Chirp z-transform (CZT) can be used for this conversion. For example, CZT has been used in this disclosure. In order to improve signal-to-noise ratio (SNR), partial noise elimination, such as baseline drift elimination, high-frequency noise elimination and catastrophe point suppression may be performed on the time-domain data before the time-frequency conversion. The filter method and/or root mean square method can be used in this disclosure for eliminating the baseline drift, the high-frequency noise and the catastrophe point. Some other methods, such as the wavelet transform method, neural network method and adaptive comb filter method, can also be used for removing the noise interference. In order to enhance the main spectral peak and reduce sidelobe interference, a window can be increased for sidelobe suppression. For instance, a Kaiser window may be used for sidelobe suppression in this disclosure.

Each spectral peak information of the frequency-domain data, i.e., frequency location $$\sum_{n=0}^{N-1} fPeak_{Freq}(n)$$

and amplitude value $$\sum_{n=0}^{N-1} fPeak_{Amp}(n),$$

may be searched and recorded. The difference transformation method and slope transformation method may be used to recognize the spectral peak information. The search may be carried out as follows: when the recognized spectral peak has a frequency beyond a physiological range of about 0.3-5 Hz, or when the recognized spectral peak has an amplitude less than that of a maximum spectral peak by about 4%, the corresponding spectral peak will be discarded.

The frequency location $$\sum_{n=0}^{N-1} fPeak_{Freq}(n)$$

and the amplitude value $$\sum_{n=0}^{N-1} fPeak_{Amp}(n)$$

may be searched once again so as to obtain the spectral peaks of the external compression frequency and the spontaneous cardiac rhythm, and they may be re-recorded as the frequency location $$\sum_{n=0}^{N-1} fPeak_{Freq}^{P}(n)$$

and the amplitude value $$\sum_{n=0}^{N-1} fPeak_{Amp}^{P}(n)$$

(p means probable peak information). The search may be carried out as follows: when a certain spectral peak has a harmonic component, a corresponding harmonic spectral peak is cancelled. The sidelobe peak of each spectral peak may be searched and deleted according to a spectral theoretical formula.

The external compression frequency should be maintained at about 110 BPM (1.83 Hz) according to CPR guidelines. Therefore, the spectral peak information of the external compression frequency, i.e., frequency location $fPeak_{Freq}^{CPR}$ and amplitude value $fPeak_{Amp}^{CPR}$, can be determined by searching the frequency location $$\sum_{n=0}^{N-1} fPeak_{Freq}^{P}(n)$$

and the amplitude value $$\sum_{n=0}^{N-1} fPeak_{Amp}^{P}(n).$$

The determination rule can be as follows: those spectral peaks of about 110 BPM±10 BPM (1.83 Hz±0.17 Hz) can be deemed as the spectral peak of the external compression frequency.

Figure 18:
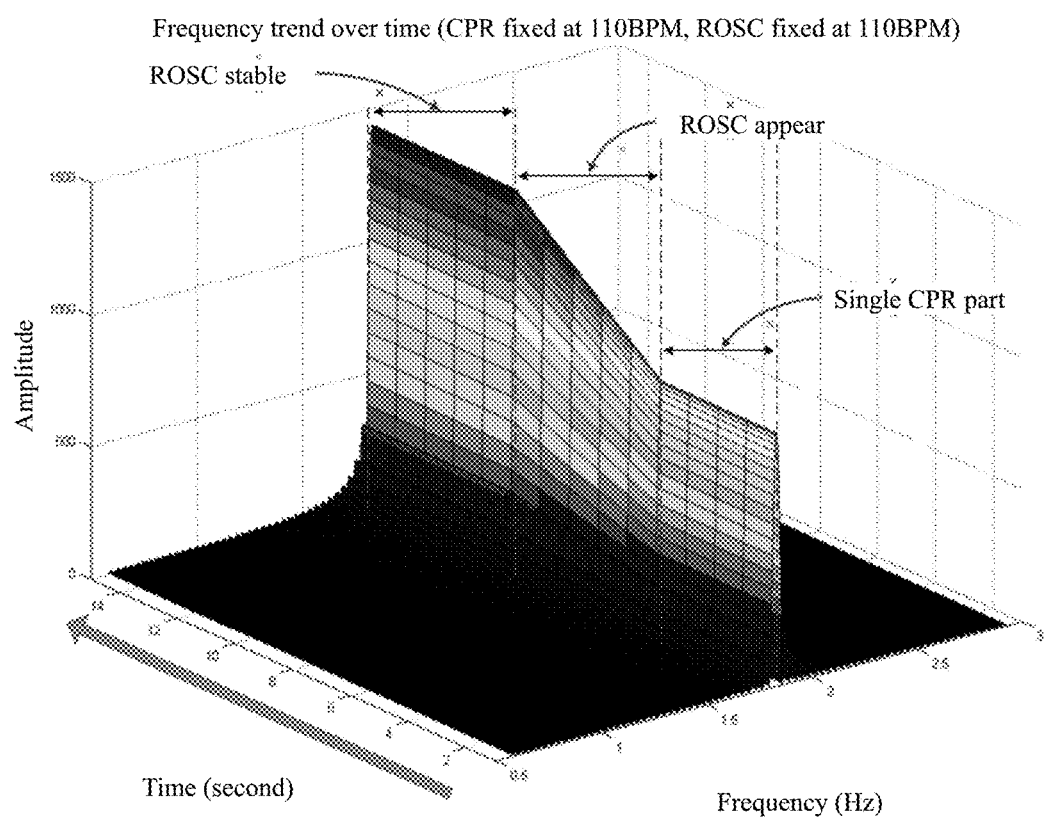
FIGS. 18-21 show variations of spectral distributions of manual compression signals and spontaneous circulation signals when applying an exemplary frequency-domain ROSC recognition logic.

A sliding time window can be established to evaluate the changes of the frequency location $fPeak_{Freq}^{CPR}$ and amplitude value $fPeak_{Amp}^{CPR}$. It can be deemed that the spontaneous cardiac rhythm and the external compression frequency are basically consistent in the following situations: the frequency is within the sliding time window and stable at about 110 BPM±10 BPM (1.83 Hz±0.17 Hz), while the amplitude value $fPeak_{Amp}^{CPR}$ has significant changes (e.g., at least about 20% fluctuations). The time duration of the sliding time window can be set according to system operation. For example, an observation time can be set to be about six to eight seconds. As shown in FIG. 18, provided that both the spontaneous cardiac rhythm and the external compression frequency are about 110 BPM (1.83 Hz), the spontaneous cardiac rhythm may occur at about the sixth second with increasing amplitude and become stable in amplitude at about the 11th second. Besides, overlapping amplitude may appear at the spectral peak due to the same frequency. FIG. 18 shows that the amplitude of the mixed frequency spectrum resulted from the spontaneous cardiac rhythm, and the compression frequency can gradually increase and finally become stable. Through the above-described sliding time window, the spontaneous cardiac rhythm can be determined by evaluating the variation characteristic of the spectral amplitude within the sliding time window.

Figure 19:
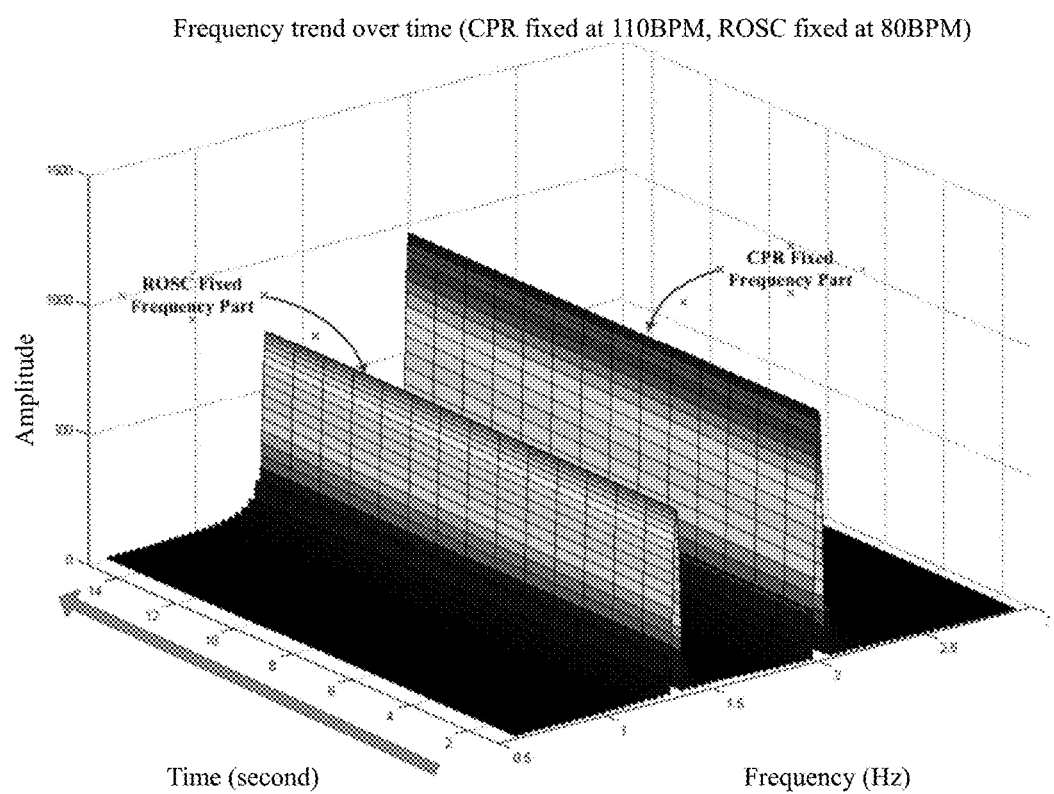

The frequency location $fPeak_{Freq}^{CPR}$ and the amplitude value $fPeak_{Amp}^{CPR}$ can be evaluated comprehensively, so that the spectral peaks (except that of the external compression) may be used as the evaluation subject. A sliding time window can be established to observe a distribution range of the frequency spectrum variations therein in every second. Within the observation period, the frequency spectrum and the amplitude of the spontaneous cardiac rhythm can be found in the frequency spectrum continuously, while other interfering spectral peaks may not show any continuous characteristics because of random distribution of white noise. Therefore, whether there is spontaneous cardiac rhythm can be determined according to such continuously stable characteristics of the spectral peak over time. The time duration of the sliding time window can be adaptively adjusted according to system features. For instance, when combining with the features of the pulse oximetry system described in this disclosure, the sliding time window may be set to about six to eight seconds. It can be determined that the spontaneous cardiac rhythm has been restored and its frequency is inconsistent with that of the external compression in the following situations: a certain spectral peak lasting for about six to eight seconds is detected, and its amplitude in the frequency spectrum per second is larger than a certain proportion of a maximum amplitude of the spectral peak of the external compression frequency. This proportion can be adjusted based on system features. A lower proportion can lead to high sensitivity but also increased risk of misrecognition. In this disclosure, a default proportion can be about 20%. As shown in FIG. 19, assuming that the spontaneous cardiac rhythm can be about 80 BPM and the external compression frequency can be about 110 BPM, the spontaneous cardiac rhythm can be recognized based on a continuous evaluation of the sliding time window.

Figure 20:
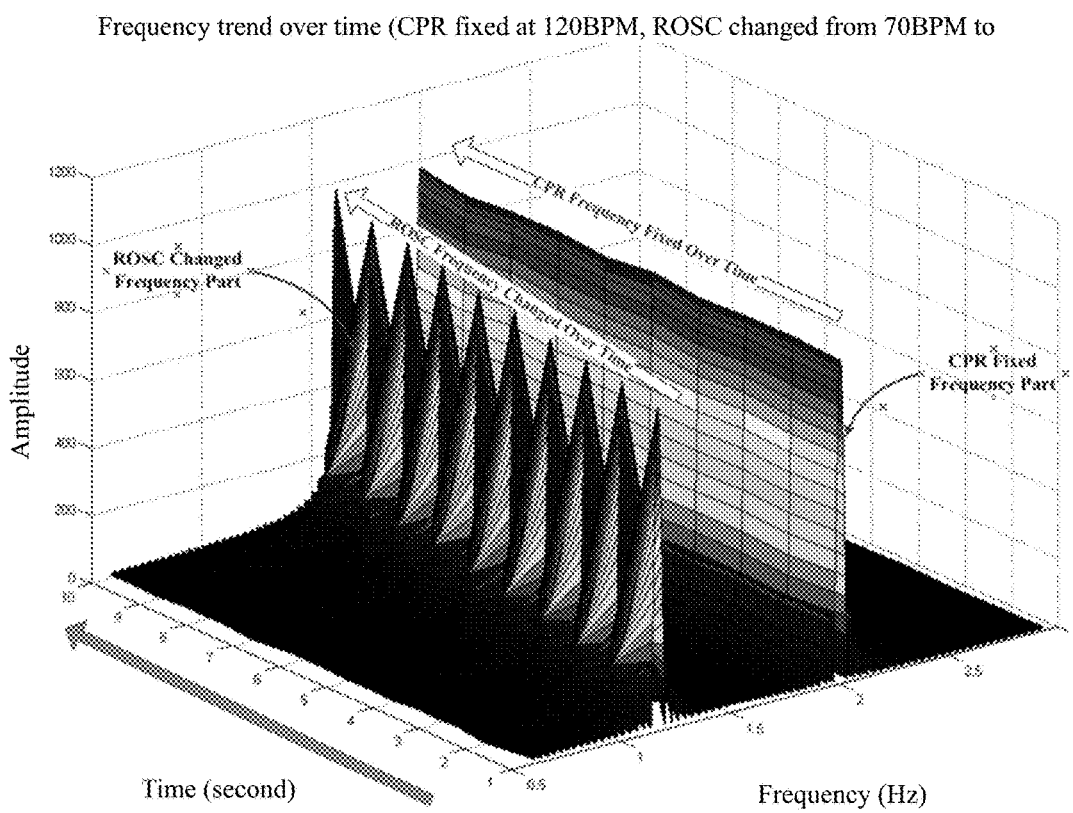

Physiological specificities have noted that the frequency of the spontaneous circulation can show a gradually increasing tendency in the compression process. For this reason, after detecting a spectral peak lasting for about six to eight seconds and having an amplitude of a certain proportion (e.g., about 20% in this disclosure) of that of the external compression frequency, a monotonicity evaluation should further be carried out on the variation tendency of the location of the spectral peak. It can be deemed that the spontaneous cardiac rhythm has been restored when all the situations above are met. Assuming that the external compression frequency is about 120 BPM (2.0 Hz), and a pulse rate of the spontaneous cardiac rhythm increases gradually from about 70 BPM to about 100 BPM (1.167 Hz-1.667 Hz) over time, the gradually increasing effect of the spontaneous cardiac rhythm in the compression process can be found in FIG. 20.

Figure 21:
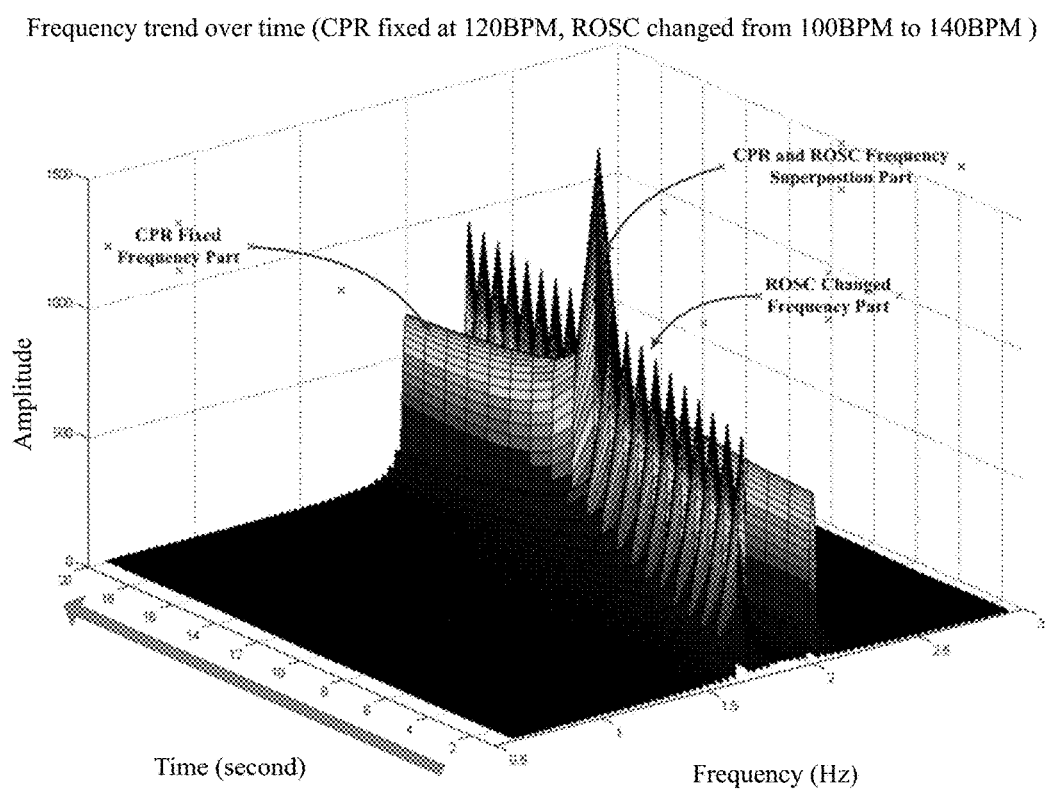

As the spontaneous cardiac rhythm increases, it may become overlapped with the external compression frequency. That is, the spontaneous cardiac rhythm and the external compression frequency may be the same at a time instant. In this case, the above-described feature recognition should be combined in the recognition process. On one hand, whether there is a continuous spectral peak in about six to eight seconds, whether its amplitude is at least a certain proportion to that of the external compression frequency, and whether this spectral peak has a monotone increasing tendency in the frequency should be evaluated. On the other hand, the amplitude variation should be evaluated for the external compression frequency. After all the situations above are met, ROSC can be determined. Assuming that the spontaneous cardiac rhythm changes from about 100 BPM to about 140 BPM (1.67 Hz-2.33 Hz) and the external compression frequency maintains at about 120 BPM (2 Hz), FIG. 21 shows how the spontaneous cardiac rhythm increases gradually and overlaps with the external compression frequency, where the overlapping amplitude can be found in the case when the two frequencies are consistent.

For restoration of spontaneous circulation during external compression, the descriptions above have illustrated how to recognize the spontaneous cardiac rhythm from time domain and frequency domain respectively. The time-domain logic can recognize the spontaneous cardiac rhythm during external compression from the shape feature of the mixed waveform that resulted from waveform superposition. The frequency-domain logic can recognize the spontaneous cardiac rhythm during external compression by evaluating whether the spontaneous cardiac rhythm and the external compression frequency can overlap with each other. The time-domain recognition may mainly depend on the shape feature, which can be non-obvious in the case of low SNR caused by motion interference or low hemoperfusion. The frequency-domain recognition may mainly depend on the frequency and amplitude information evaluation based on the frequency spectrum, thus exhibiting good anti-interference capability. Therefore, for the purpose of improving reliability and stability, ROSC may be evaluated comprehensively during external compression based on the frequency-domain analysis while combining with the time-domain analysis. Alternatively, the frequency-domain or the time-domain analysis can be used independently for ROSC recognition during external compression.

Through a large number of external compression data in animal experiments, the above-described methods can realize the ROSC recognition during external compression very well. At this point, the following feature points may further be defined in combination with the variations of the clinical physiological features.

Provided that the spontaneous cardiac rhythm and the external compression frequency are inconsistent with each other, the patient may have good ROSC when the amplitude of the spectral peak of the spontaneous cardiac rhythm is larger than or equal to the spectral peak amplitude of the external compression. For this reason, fRatio can be established:

$$fRatio(n) = \frac{fPeak_{Amp}^{ROSC}(n)}{fPeak_{Amp}^{CPR}(n)},$$

where fRatio represents a ratio at an nth second between the amplitudes of the spectral peaks of the spontaneous cardiac rhythm and the CPR.

A probability when the fRatio is continuously larger than or equal to 1.0 is counted in a sliding time window of about six to eight seconds. When the probability is at least about 75% (which can be adaptively adjusted according to system features), the ROSC and the restoration condition can be determined. In this way, some technical prompt and/or warning information can be provided based on the determination results.

Provided that the spontaneous cardiac rhythm and the external compression frequency are basically consistent with each other, the amplitude of the spectral peak resulting from peak overlapping may decrease. For this reason, both the increasing and the decreasing tendencies of the amplitude of the spectral peak should be evaluated in the event that spontaneous cardiac rhythm and external compression frequency are consistent. In the sliding time window of about six to eight seconds, the ROSC can be determined when the amplitude of the spectral peak of the external compression decreases continuously by about 25%-60% (when compared with the amplitude at an initial moment of the sliding time window) and its corresponding decreasing duration accounts for at least about 70% (which can be adaptively adjusted according to system features) of the sliding time window. In this way, some technical prompt and/or warning information can be provided based on the determination results to avoid any cardiac damage.

Although the spontaneous cardiac rhythm can be restored through the CPR emergency treatment, the spontaneous circulation may be unstable and the cardiac arrest may happen again because of ischemia, hypoxia and reperfusion injury of the heart and microcirculation in the CPR process. Once failing to detect such unstable condition or cardiac arrest, an optimal rescue time may be delayed. Therefore, in order to find and warn of any unstable spontaneous circulation for timely treatment, an evaluation and feedback system for circulation quality should be established after ROSC is determined. In this disclosure, a practical mechanism for quality evaluation of the spontaneous cardiac rhythm can be established according to the features of the spontaneous cardiac rhythm. Post-ROSC circulation quality evaluation which may also be called ROSC quality for short will be described in detail below.

For system sampling signals, the pulse waves formed by the external compression and the spontaneous circulation are basically consistent with each other, where their difference may be whether the cardiac motion is caused by manual compression or spontaneous circulation. Based on this point, a series of parameters for evaluating compression quality disclosed in a patent application CN201310474008.7 can also be used for the quality evaluation of the spontaneous circulation. This disclosure describes how to evaluate the quality of restoration of the spontaneous cardiac rhythm using PVPI parameters disclosed in the patent application CN201310474008.7 as an example.

Figure 22:
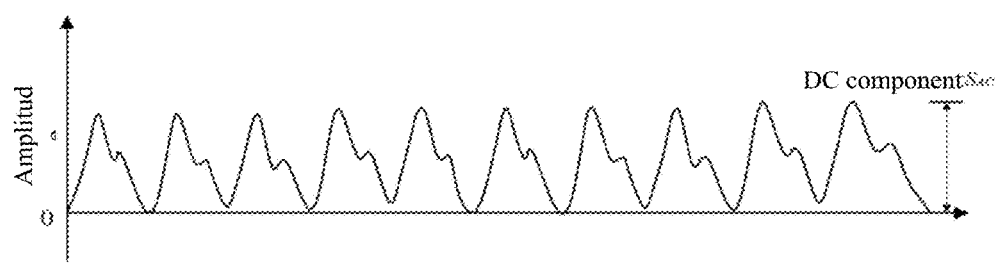
FIG. 22 is a schematic diagram for AC components of blood oxygen signals sampled from a patient.

Original signals I can include AC components $S_{AC}$ and DC components $S_{DC}$. In some cases, certain factors such as body movement and background light interference may result in a drift of the DC components $S_{DC}$ over time, namely its numerical value may not be constant but can fluctuate with time. By using suitable technologies such as average value technology, smooth filtering technology, finite impulse response digital filter/infinite impulse response digital filter (FIR/IIR) filtering technology or curve fitting technology, the DC components $S_{DC}$ can be filtered out of the original signals I and the AC components $S_{AC}$ can be left for further data processing. FIG. 22 shows the AC components $S_{AC}$ after filtering out the DC components $S_{DC}$.

The AC components $S_{AC}$ may be related to blood flow, and its frequency can be consistent with the CPR compression frequency. The frequency of the AC components $S_{AC}$ can be multiplied by 60, so as to obtain the blood oxygen frequency, namely CPR compression times per minute.

$$F_{ROSC} = F_{S_{AC}}$$

where $F_{ROSC}$ represents the CPR compression frequency, $F_{S_{AC}}$ represents the frequency of the AC components $S_{AC}$, and the unit of both is Hertz (Hz).

$$Deg_{ROSC} = F_{ROSC} * 60 = F_{S_{AC}} * 60$$

where $Deg_{ROSC}$ represents the CPR compression times per minute, and its unit is time per minute.

By combining Deg$_{ROSC}$ and ECG, electrical mechanical dissociation or severe peripheral circulatory failure can be detected on the patient.

It is known from Parseval theorem that there can be energy conservation between time domain and frequency domain, and thus those parameters described below can be calculated by two methods, i.e., the time-domain method and the frequency-domain method.

Area characteristics of each pulse wave of the AC components $S_{AC}$ can be calculated to evaluate the variations of the stroke volume of the spontaneous cardiac rhythm so that the quality of restoration of the spontaneous cardiac rhythm can be reflected indirectly. The area value of each pulse wave can be calculated by any suitable technologies such as the area integral method, which may be applicable to both continuous signals and discrete signals. In this embodiment, based on the features of fixed sampling frequency of blood oxygen technology, the method of point-by-point accumulation integral can be used to calculate the area parameter.

Formula in time domain:

$$Area_{ROSC} = \sum_{n=0}^{N-1} S_{AC}(n)$$

where $S_{AC}(n)$ represents the nth sampling data point of each pulse wave, n represents the current data point of the single pulse wave, and N represents the total data length of the single pulse wave. Area$_{ROSC}$ can be a stroke volume parameter, and its unit can be defined as PVPG (Pulse Oximeter Voltage Plethysmography), which is also called voltage volume.

Formula in frequency domain:

$$Area^*_{ROSC} = \sum_{n=0}^{N-1} \left( \sum_{k=0}^{K-1} X_{fn}(k) \right)$$

where Area*$_{ROSC}$ can be a stroke volume parameter, and its unit can be defined as PVPG (Pulse Oximeter Voltage Plethysmography), which is also called voltage volume, n represents the current effective frequency component $f_n$, N represents the total number of the effective frequency components, k represents the data point of the current effective frequency $f_n$, and K represents the total data length of the effective frequency component $f_n$.

The parameters Area$_{ROSC}$ and Area*$_{ROSC}$ can reflect the stroke volume indirectly, which means they are not directly equal to the stroke volume. In theory, they should exhibit a linear positive correlation with the cardiac ejection volume in every compression.

Figure 23:
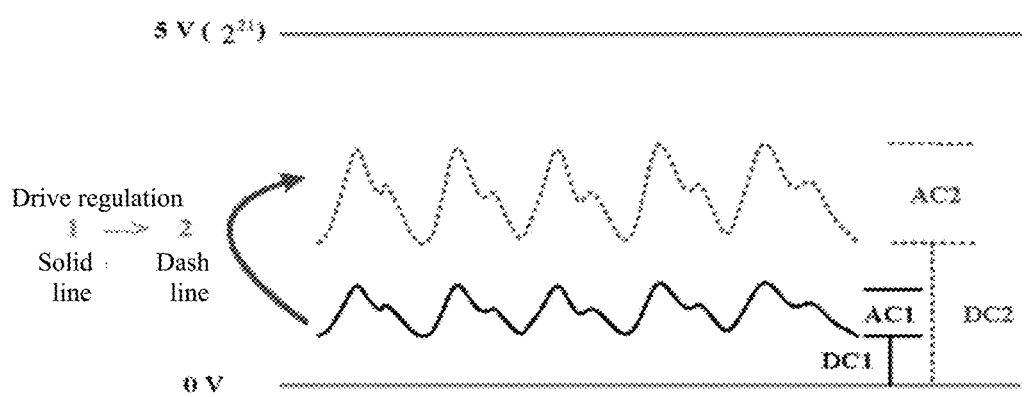
FIG. 23 is a schematic diagram illustrating a drive current regulation of sampled blood oxygen signals.

According to the characteristics of the blood oxygen system, drive current regulation should be performed depending on the signal conditions, so as to make the sampled blood oxygen signals fall within a measurable range. As shown in FIG. 23, the variations of the drive current can lead to the changes of the AC components and the DC components by the same rate. In FIG. 23, the signal in the solid line falls within a lower measurement range. In this case, drive regulation can be made so that the signals would fall within a reasonable measurement range. For example, after a double drive regulation, the signal in dotted line as shown in FIG. 23 locates at a middle position of the measurement range. According to the drive characteristic, it is known that AC2=AC1*2 and DC2=DC1*2.

As a result, the above-described PVPG parameters, i.e., Area$_{ROSC}$ and Area*$_{ROSC}$, can further be transformed as follows when referring to the changes of the corresponding DC components of the pulse wave:

Formula in time domain:

$$AreaIndex_{ROSC} = \frac{Area_{ROSC}}{\left( \sum_{n=0}^{N-1} S_{DC}(n) \right)/N} = \frac{\sum_{n=0}^{N-1} S_{AC}(n)}{\left( \sum_{n=0}^{N-1} S_{DC}(n) \right)/N}$$

where AreaIndex$_{ROSC}$ refers to a CPR quantization index which can be defined as the voltage volume index, and its unit can be PVPI (Pulse Oximeter Voltage Amplitude Index).

Formula in frequency domain:

$$AreaIndex^*_{ROSC} = \frac{Area^*_{ROSC}}{\left( \sum_{n=0}^{N-1} S_{DC}(n) \right)/N} = \frac{\sum_{n=0}^{N-1} \left( \sum_{k=0}^{K-1} X_{fn}(k) \right)}{\left( \sum_{n=0}^{N-1} S_{DC}(n) \right)/N}$$

where AreaIndex*$_{ROSC}$ refers to a CPR quantization index which can be defined as the voltage volume index, and its unit can be PVPI (Pulse Oximeter Voltage Amplitude Index).

The parameters AreaIndex$_{ROSC}$ and AreaIndex*$_{ROSC}$ can be ratios between the area value and its corresponding DC components of the single pulse wave, thus being capable of reducing the individual difference, removing the interference from drive regulation and having sound anti-interference capacity.

The parameters AreaIndex$_{ROSC}$ and AreaIndex*$_{ROSC}$ can reflect the variation of the cardiac stroke volume. It is known from the physiological features that the stroke volume may have a minimum output. The body's peripheral blood circulation is poor or even fails to meet normal physiological needs when the stroke volume is lower than its minimum output. Based on such physiological features, there may be minimum area index thresholds for the parameters AreaIndex$_{ROSC}$ and AreaIndex*$_{ROSC}$. If these parameters are lower than those thresholds, the body may exhibit poor spontaneous cardiopulmonary quality and fail to meet the normal physiological needs. In case the stroke volume is unstable, or it gradually reduces and even stops over time, the indexes AreaIndex$_{ROSC}$ and AreaIndex*$_{ROSC}$ may have large fluctuations in their parameter values or they may decrease and even disappear over time. Based on these features, the post-ROSC circulation quality can be recognized and evaluated effectively.

In order to evaluate the post-ROSC circulation quality, a sliding time window may be established so that the time-varying fluctuating characteristics of the parameters AreaIndex$_{ROSC}$ and AreaIndex*$_{ROSC}$ can be evaluated in combination with a lowest physiological threshold. The time duration of the sliding time window can be adaptively adjusted according to system features. For example, it can be set as about four to six seconds. The spontaneous circulation under the spontaneous cardiac rhythm may be unstable when the parameters for spontaneous cardiac rhythm AreaIndex$_{ROSC}$ and AreaIndex*$_{ROSC}$ have significant fluctuations or decrease gradually. Specifically, the unstable spontaneous circulation under the spontaneous cardiac rhythm can be determined in the following situation: the parameters in the sliding time window may decrease by about 20% relative to an average value in 30 seconds in an initial stage of the spontaneous cardiac rhythm, where the value of the parameters can be recognized on average value and standard deviation, and the fluctuating proportion can be adaptively adjusted according to system requirements; or the parameters may exhibit a time-dependent decreasing tendency and have a maximum decrease by about 30% (which can be adaptively adjusted according to system requirements). At this point, some prompt and/or warning information can be provided so that a doctor can be guided to make an immediate decision to avoid further damage.

Figure 24:
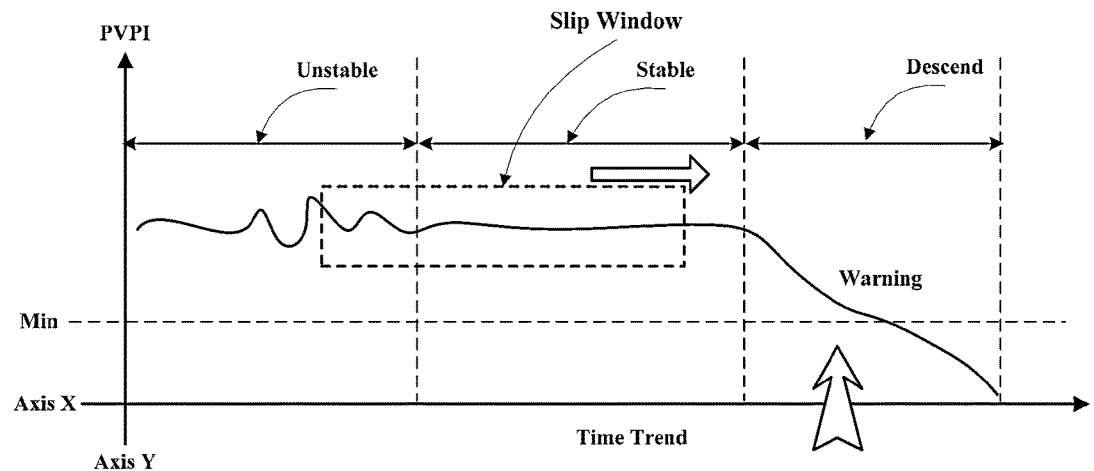
FIG. 24 shows a quality evaluation for spontaneous cardiac rhythm when taking cardiac stroke volume as an example.

FIG. 24 is a schematic diagram showing the quality evaluation of the spontaneous cardiac rhythm by using the parameter AreaIndex*$_{ROSC}$ as an example. The "unstable stage" shows that the parameters may be fluctuating, where some prompt and/or warning information can be provided when the fluctuation is larger than about 20%. The "stable stage" shows that the parameters may be relatively stable, and prompt information can be provided to show sound cardiac rhythm of the spontaneous circulation. The "decreasing stage" shows that the parameters may be decreasing, where some prompt and/or warning information can be provided when it has decreased by at least about 20%. Specifically, another prompt and/or warning information can be provided when the parameters are lower than the threshold line for a certain time. The "Sliding window" in FIG. 24 can stand for the sliding time window which can slide over time. The fluctuating characteristics of the parameters can be evaluated in the time window, so that the quality evaluation of the spontaneous cardiac rhythm can be analyzed, and some corresponding prompt and/or warning information can be provided.

Another index for the quality of the spontaneous circulation is pulse rate. The pulse rate can indicate the true tissue perfusion state, while the heart rate shown by ECG activity can represent the cardiac electric activity rhythm. Under the condition of sound spontaneous circulation, the pulse rate should be basically consistent with the heart rate, thereby avoiding severe fluctuations and falling within a reasonable range. Once the pulse rate decreases continuously by more than about 5% per second relative to the heart rate, becomes lower than about 60 times per minute, or seems much smaller when compared to the heart rate, the spontaneous circulation may be in an unstable state. There may be electrical mechanical dissociation or severe peripheral circulation failure in the case when ECG heart rate is detected without pulse rate. In this case, the spontaneous circulation under the spontaneous cardiac rhythm can be deemed to be unstable, which needs to be dealt with immediately. Also, some prompt and/or warning information may be provided so that the doctor can be guided timely to make a decision to avoid further damage.

Figure 25:
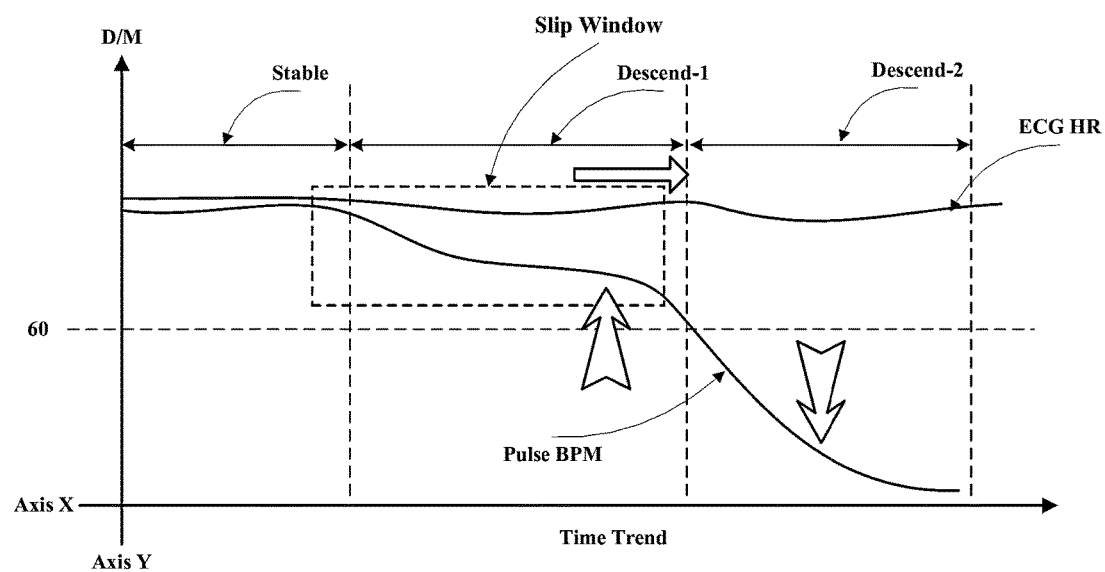
FIG. 25 shows a quality evaluation for spontaneous cardiac rhythm when taking pulse rate as an example.

As shown in FIG. 25, "ECG HR" is a trend line for the ECG heart rate, and "pulse BPM" is a trend line for the ROSC pulse rate. A sliding time window can be established to evaluate the differences between the ECG heart rate and the ROSC pulse rate within this time window. There may be prompt/warning information when the ROSC pulse rate is detected to decrease by about 5% (which is a ratio between the ROSC pulse rate and the ECG heart rate), or when the ROSC pulse rate is detected to be lower than about 60 times per minute. In FIG. 25, the "stable stage" indicates consistent ECG heart rate and ROSC pulse rate, the "decreasing-1 stage" shows the dissociation of ROSC pulse rate and ECG heart rate in which an electrical mechanical dissociation may appear, and the "decreasing-2 stage" shows that the ROSC pulse rate is continuously lower than about 60 times per minute. During the sliding process of the sliding time window, the variations of the ECG heart rate and the ROSC pulse rate can be evaluated therein. Once the "decreasing-1 stage" or "decreasing-2 stage" is detected, a warning/prompting message, such as the two arrows pointing to positive and negative directions of the Y axis in FIG. 25, can be provided.

Based on the descriptions above, ROSC recognition devices for real-time recognition of ROSC in a CPR process, systems for recognition and quality evaluation of ROSC, ROSC feedback systems in a CPR process, and ROSC recognition devices without external compression after defibrillation can be provided.

Figure 26:
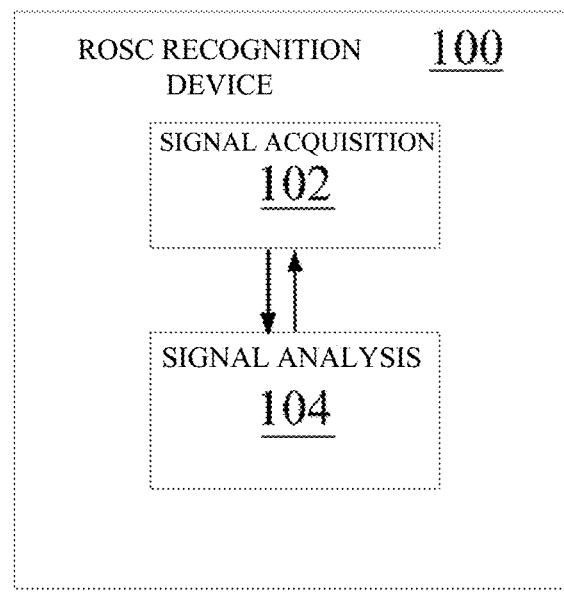
FIG. 26 is a block diagram for an ROSC recognition device for real-time recognition of ROSC in a CPR process according to an embodiment of this disclosure.

FIG. 26 is a block diagram for an ROSC recognition device 100 for real-time recognition of ROSC in a CPR process according to an embodiment of this disclosure. The ROSC recognition device 100 may include a signal acquisition apparatus 102 and a signal analysis apparatus 104. The signal acquisition apparatus 102 can be used to acquire pulse oximetry waveform signals of a patient. The signal analysis apparatus 104 can be used to analyze these signals to determine whether there is ROSC in the CPR process.

In one embodiment, the signal acquisition apparatus 102 can include a receiving tube and a light-emitting tube as shown in FIG. 1. In this way, it can convert detected red light and/or infrared light penetrating through finger arteries into electrical signals so as to obtain the pulse oximetry waveform signals of the patient.

In one embodiment, the signal analysis apparatus 104 can include the above-described exemplary time-domain recognition logic and/or frequency-domain recognition logic. The time-domain recognition logic can be used to recognize whether there is ROSC in the CPR process by detecting the time-domain envelope of the sampled signals. The frequency-domain recognition logic can be used to recognize whether there is ROSC in the CPR process by detecting the time-varying features of the spectral peak of the sampled signals. For the time-domain recognition logic, ROSC can be determined when the continuous envelope feature is recognized; while for the frequency-domain recognition logic, ROSC can be determined when spectral peaks are recognized continuously at different frequencies or significant change in the amplitude of the spectral peak is recognized within a certain time.

In one embodiment, the signal analysis apparatus 104 can include two parts: an algorithm software program and a hardware environment such as a programmable logic device for the running of the algorithm software program. The programmable logic device may be a flash memory or a RAM. Other suitable programmable logic devices such as the Cortex series can also be used as a carrier for the algorithm software program.

Figure 27:
FIG. 27 shows an example for a shape factor of the ROSC recognition device of FIG. 26 when it is implemented as a one-parameter medical equipment.

In one embodiment, the ROSC recognition device 100 can be a function module which may be integrated with any other auxiliary diagnostic equipment (e.g., monitoring device, defibrillator, automatic external defibrillator (AED), automatic resuscitator equipment and electrocardiograph) as a plug-in unit. Alternatively, the ROSC recognition device 100 can be a one-parameter medical equipment for the recognition of the spontaneous cardiac rhythm during the external compression. For instance, the one-parameter medical equipment can have the shape factor shown in FIG. 27.

Figure 28:
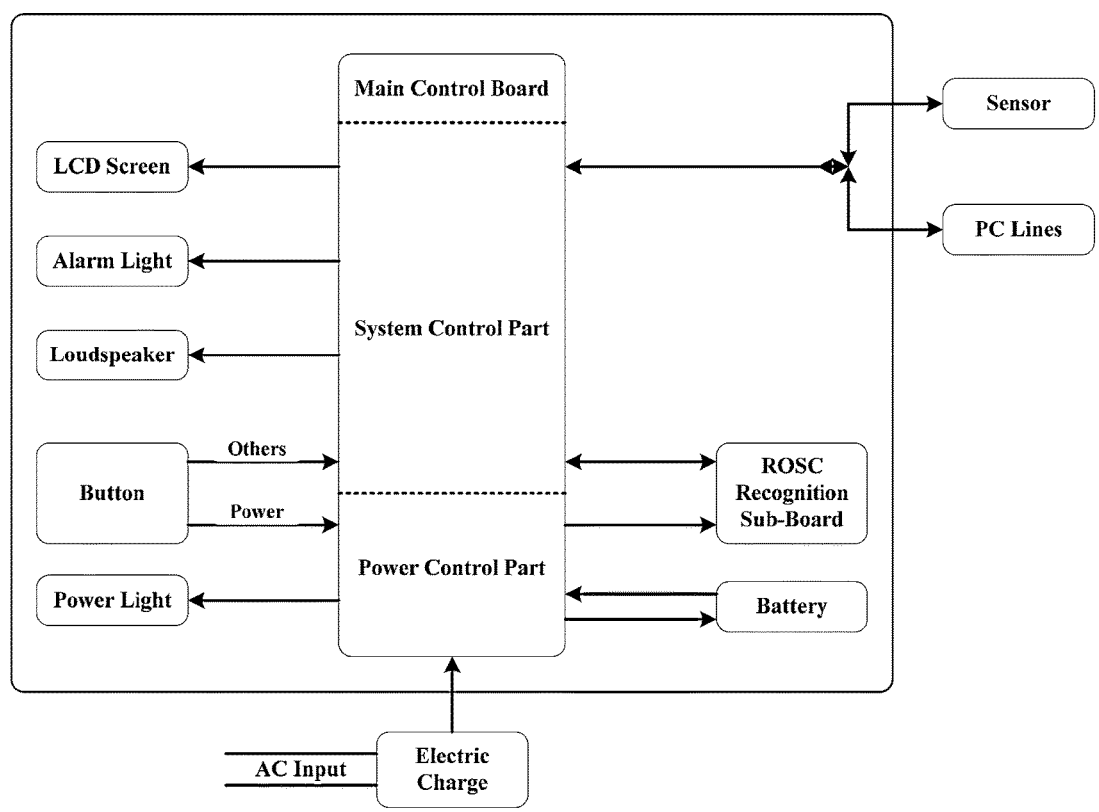
FIG. 28 is a schematic diagram for exemplary hardware of the ROSC recognition device shown in FIG. 26.

FIG. 28 is a schematic diagram for exemplary hardware of the ROSC recognition device shown in FIG. 26. Specifically, the ROSC recognition device may include a main control panel, an ROSC recognition sub-board, a display (e.g., an LCD screen), a loudspeaker, a battery, a charger and an indicator lamp. Herein, the main control panel may include two parts: a system control part and a power control part. The ROSC recognition sub-board may function as a source of all the system parameters. It can acquire physiological signals, perform calculations on the physiological signals, output some related parameters and have a communication interface with a control system.

Figure 29:
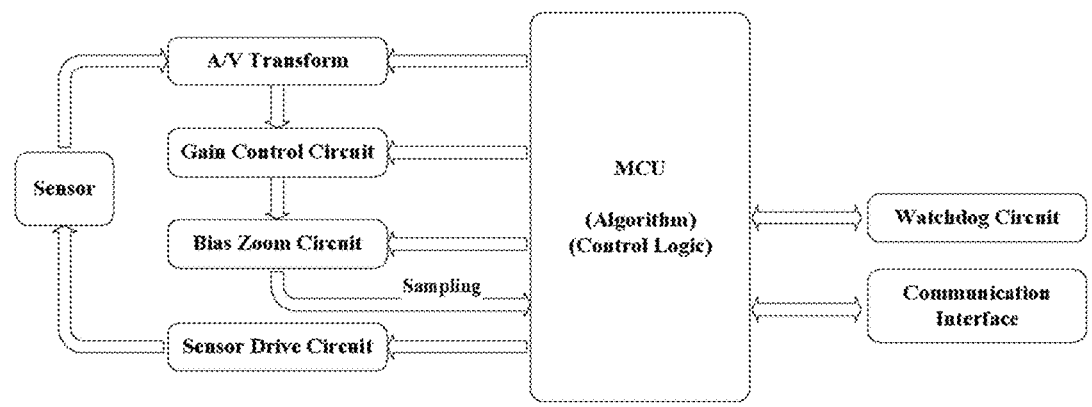
FIG. 29 is an example circuit diagram for an ROSC recognition sub-board in the ROSC recognition device of FIG. 28.

FIG. 29 is a schematic circuit diagram for the above-described ROSC recognition sub-board. The ROSC recognition sub-board may include a micro-programmed Control Unit (MCU) chip, a watchdog circuit, a communication interface, an I/V conversion circuit, a gain control circuit, a bias zoom circuit, a sensor drive circuit and sensors. The MCU chip can include ROSC recognition algorithms and peripheral control logics.

Figure 30:
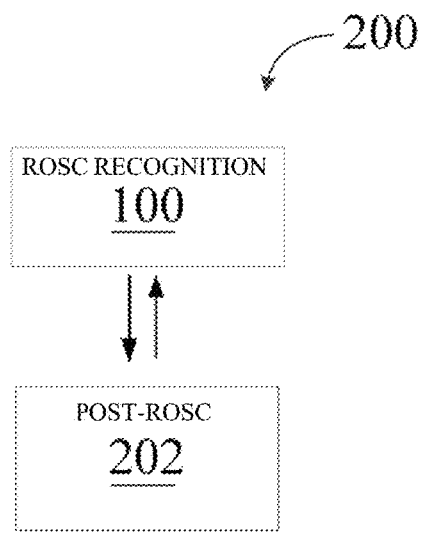
FIG. 30 is a block diagram for an ROSC recognition and post-ROSC circulation quality evaluation system according to an embodiment of this disclosure.

FIG. 30 is a block diagram for an ROSC recognition and post-ROSC circulation quality evaluation system 200 according to an embodiment of this disclosure. This system 200 may include the ROSC recognition device 100 shown in FIG. 26 and a post-ROSC circulation quality evaluation apparatus 202 for quality evaluation of ROSC.

In one embodiment, the post-ROSC circulation quality evaluation apparatus 202 may be used to evaluate the post-ROSC circulation quality based on the variations of the cardiac stroke volume within a certain period. After ROSC is determined by the ROSC recognition device, the post-ROSC circulation quality evaluation apparatus 202 may further calculate an area characteristic of AC components of pulse signals sampled by the ROSC recognition device, so as to evaluate the changes of the stroke volume under the spontaneous cardiac rhythm and thus give indirect indication on the quality of restoration of spontaneous cardiac rhythm. Alternatively, the post-ROSC circulation quality evaluation apparatus 202 may evaluate the post-ROSC circulation quality based on the variations of pulse rate as described above.

In one embodiment, the ROSC recognition and post-ROSC circulation quality evaluation system 200 can be a function module which may be integrated with any other auxiliary diagnostic equipment (e.g., monitoring device, defibrillator, AED, automatic resuscitator equipment and electrocardiograph) as a plug-in unit. Alternatively, the ROSC recognition and post-ROSC circulation quality evaluation system 200 can be one-parameter medical equipment for the recognition of the spontaneous cardiac rhythm during the external compression. For instance, the one-parameter medical equipment can also have the shape factor shown in FIG. 27.

Figure 31:
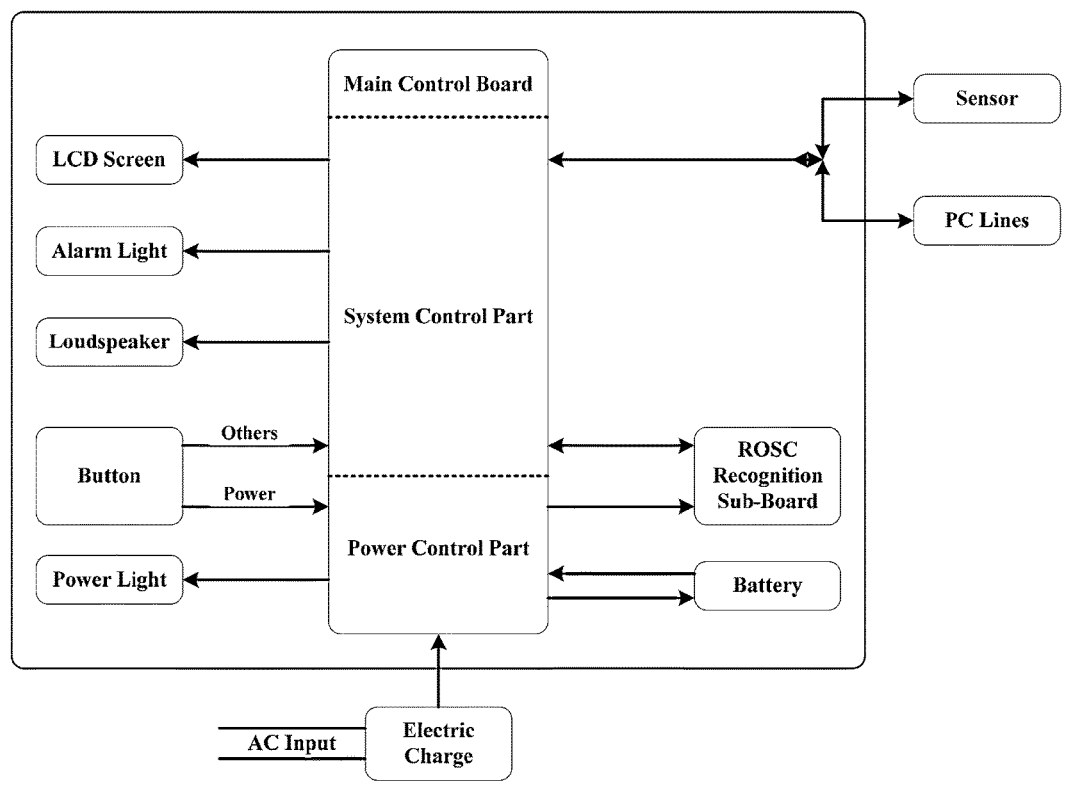
FIG. 31 is a schematic diagram for exemplary hardware of the ROSC recognition and post-ROSC circulation quality evaluation system shown in FIG. 30.

FIG. 31 is a schematic diagram for exemplary hardware of the ROSC recognition and post-ROSC circulation quality evaluation system shown in FIG. 30. Specifically, the ROSC recognition and post-ROSC circulation quality evaluation system may include a main control panel, an ROSC recognition and post-ROSC circulation quality evaluation sub-board, a display (e.g., an LCD screen), a loudspeaker, a battery, a charger and an indicator lamp. Herein, the main control panel may include two parts: a system control part and a power control part. The ROSC recognition and post-ROSC circulation quality evaluation sub-board may function as a source of all the system parameters. It can acquire physiological signals, perform calculations on the physiological signals, output some related parameters and have a communication interface with a control system. The ROSC recognition and post-ROSC circulation quality evaluation sub-board in this embodiment may have the same function as the ROSC recognition sub-board shown in FIG. 31.

Figure 32:
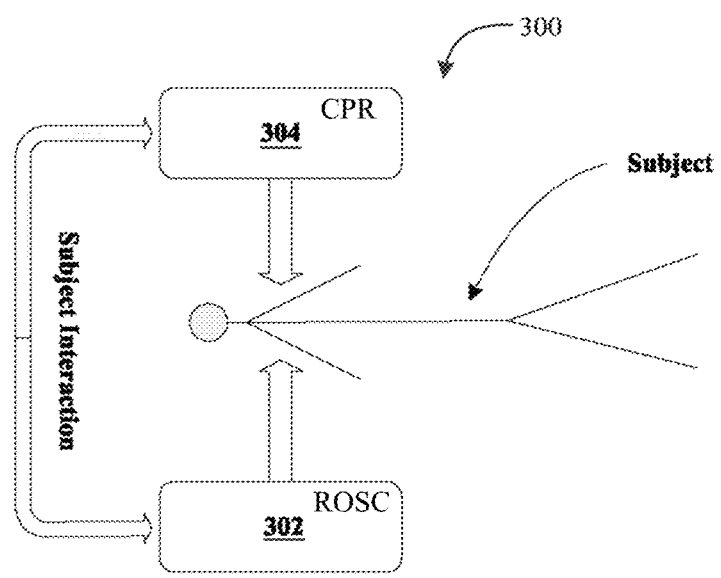
FIG. 32 is a schematic diagram for an ROSC feedback system in a CPR process according to an embodiment of this disclosure.
Figure 33:
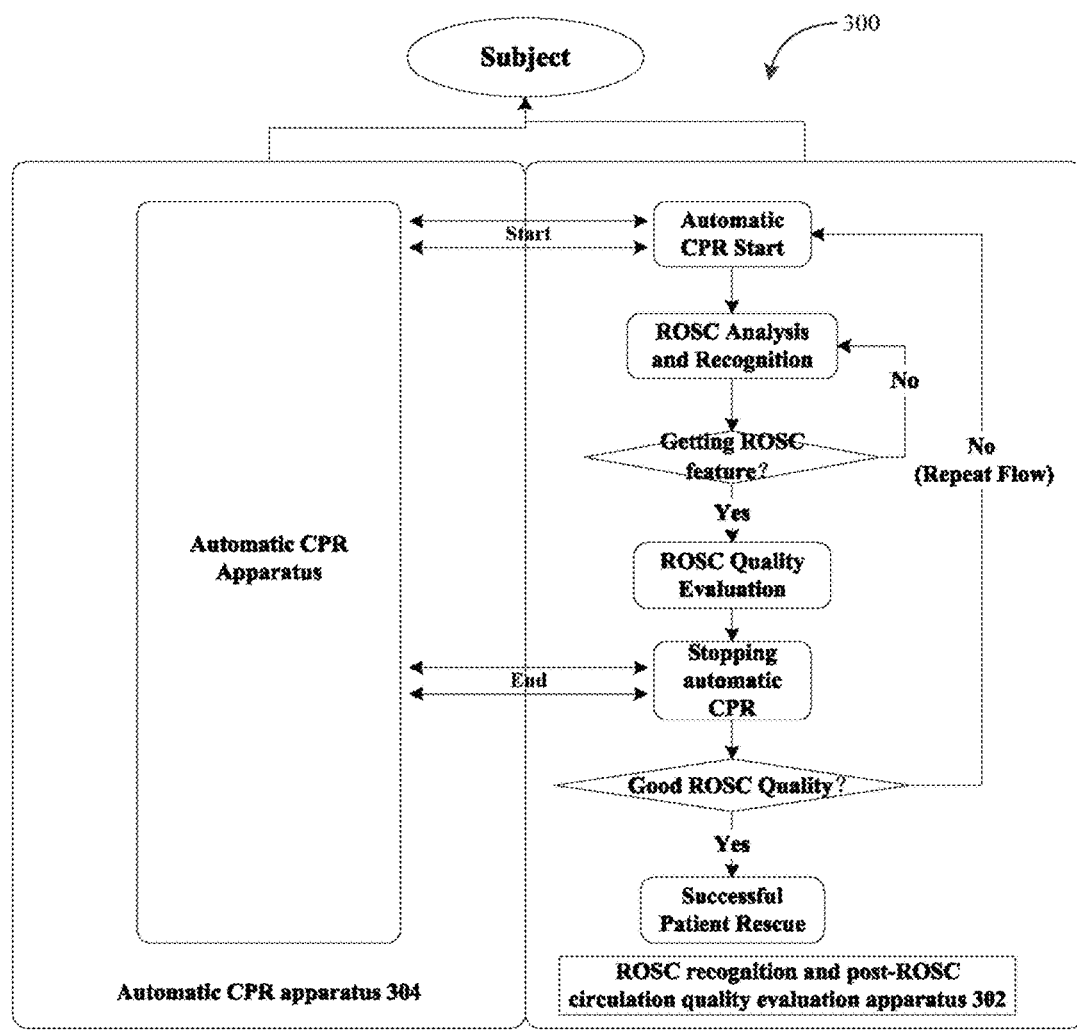
FIG. 33 shows detailed internal interactions of the system shown in FIG. 32 during operation.

FIG. 32 is a schematic diagram for an ROSC feedback system 300 in a CPR process according to an embodiment of this disclosure. This system 300 may include an ROSC recognition and post-ROSC circulation quality evaluation apparatus 302 and a CPR apparatus 304 respectively connected to a patient's body. For example, the CPR apparatus 304 can be connected to a patient's chest, and the ROSC recognition and post-ROSC circulation quality evaluation apparatus 302 can be connected to a patient's finger, forehead or other parts suitable for carrying a probe. The ROSC recognition and post-ROSC circulation quality evaluation apparatus 302 can be used to find out whether a patient has ROSC in the CPR process, and to evaluate the post-ROSC circulation quality thereafter. In this process, the CPR apparatus 304 can be used to provide compression output on the patient. The ROSC recognition and post-ROSC circulation quality evaluation apparatus 302 and the CPR apparatus 304 can operate on the human body through data interaction to realize automatic compression rescue and the ROSC recognition and post-ROSC circulation quality evaluation during the compression process. Specifically, the ROSC recognition and post-ROSC circulation quality evaluation apparatus 302 can control the CPR apparatus 304 to stop its compression output and then start the post-ROSC circulation quality evaluation when ROSC is determined. Subsequently, when the post-ROSC circulation quality is evaluated to be unstable, the ROSC recognition and post-ROSC circulation quality evaluation apparatus 302 may control (or signal) the CPR apparatus 304 to re-start its compression output, and it may perform the ROSC recognition once again. FIG. 33 gives detailed internal interaction during the operation of the system shown in FIG. 32.

The ROSC recognition and post-ROSC circulation quality evaluation apparatus 302 may follow and lock the compression frequency according to the frequency settings of the CPR apparatus 304. Meanwhile, it can detect the time-domain envelope and/or the time-varying features of the spectral peak in the frequency spectrum in real time. In one embodiment, the ROSC recognition and post-ROSC circulation quality evaluation apparatus 302 can include the exemplary time-domain recognition logic and/or the exemplary frequency-domain recognition logic described above. The time-domain recognition logic can be used to detect the time envelopes of the sampled signals in the time domain so as to recognize whether there is ROSC in the CPR process, while the frequency-domain recognition logic can be used to detect the time-varying features of the spectral peak of the sampled signals in the frequency domain so as to recognize whether there is ROSC in the CPR process. The time-domain recognition logic may determine that there is ROSC when continuous and regular envelope features are recognized. The frequency-domain recognition logic can determine that there is ROSC when spectral peaks are recognized continuously at different frequencies or significant change in the amplitude of the spectral peak is recognized within a certain time.

The system 300 may control the CPR apparatus 304 to output an acceptable compression frequency and compression depth for the corresponding patient according to the parameter information provided by the ROSC recognition and post-ROSC circulation quality evaluation apparatus 302, thereby improving the patient's survival chance. Once the ROSC recognition and post-ROSC circulation quality evaluation apparatus 302 finds stable ROSC, the whole system may be stopped to avoid any damage to the patient's cardiac functions.

Figure 34:
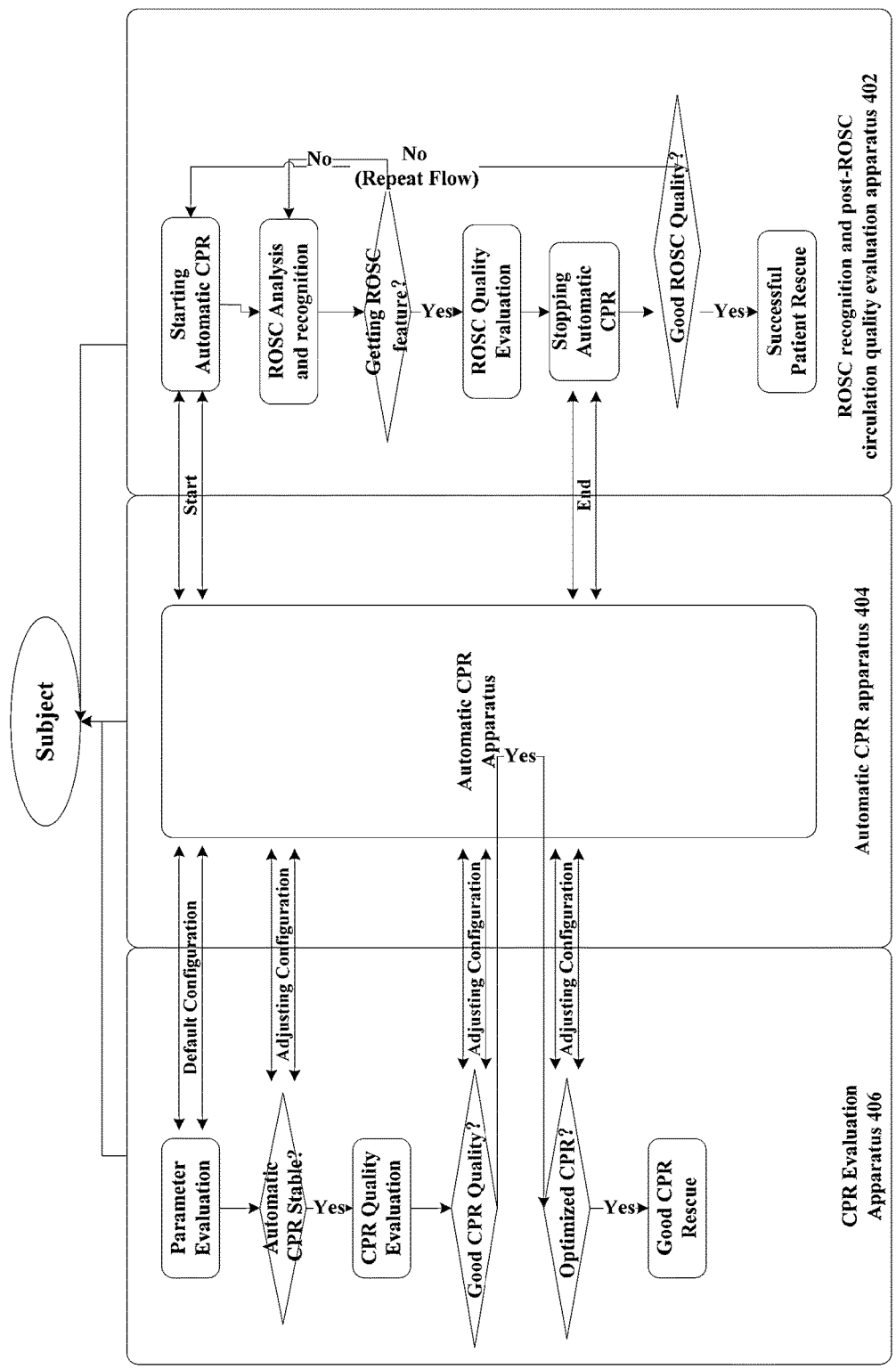
FIG. 34 shows detailed internal interactions of an ROSC feedback system in a CPR process during operation according to another embodiment of this disclosure.

According to another embodiment of this disclosure, an ROSC feedback system in a CPR process 400 can be provided. In addition to an ROSC recognition and post-ROSC circulation quality evaluation apparatus 402 and a CPR apparatus 404 like those in the system 300, this system 400 may also include a CPR quality evaluation apparatus 406. In operation, the ROSC recognition and post-ROSC circulation quality evaluation apparatus 402 can control the CPR apparatus 404 to stop its compression output and then start the post-ROSC circulation quality evaluation when ROSC is determined. Subsequently, when the post-ROSC circulation quality is evaluated to be unstable, the ROSC recognition and post-ROSC circulation quality evaluation apparatus 402 may control the CPR apparatus 404 to re-start its compression output, and it may perform the ROSC recognition once again. During the operation of the CPR apparatus 404, the CPR quality evaluation apparatus 406 can interact with the CPR apparatus 404 to recognize the CPR compression condition and provide feedback to control the CPR apparatus 404 to have an effective compression output. FIG. 34 shows the detailed internal interaction while the system 400 operates.

Figure 35:
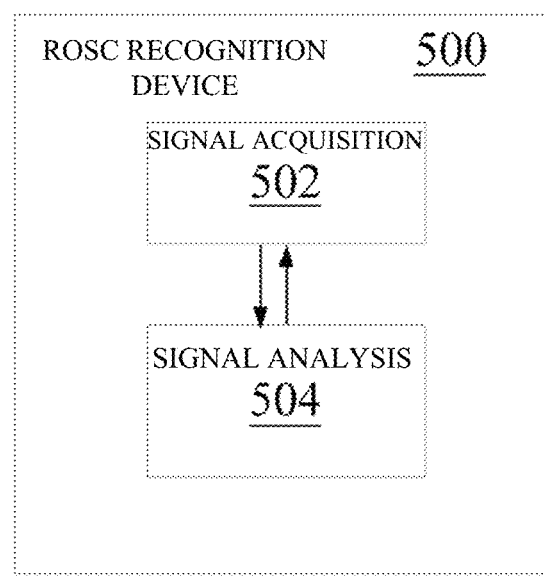
FIG. 35 is a block diagram for an ROSC recognition device without external compression after defibrillation according to an embodiment of this disclosure.

FIG. 35 is a block diagram of an ROSC recognition device without external compression after defibrillation 500 according to an embodiment of this disclosure. The device 500 may include a signal acquisition apparatus 502 for acquiring a patient's pulse wave signals and a signal analysis apparatus 504 for performing real-time analysis on these signals to determine whether there is ROSC after the defibrillation.

In one embodiment, the signal acquisition apparatus 502 can acquire the patient's pulse wave signals through red light and/or infrared light. For example, the apparatus 502 may include a receiving tube and a light-emitting tube as shown in FIG. 1. In this way, the apparatus 502 can convert detected red light and/or infrared light penetrating through finger arteries into electrical signals so as to obtain the pulse wave signals of the patient.

In one embodiment, the signal analysis apparatus 504 can be used to determine whether there is ROSC after defibrillation as shown in FIG. 5. In one embodiment, in order to eliminate noise interference beyond the physiological frequency band, the signal analysis apparatus 504 can be used to perform real-time filtering on the signals by a band pass filter before analysis. In one embodiment, the signal analysis apparatus 504 can establish a sliding time window for the sampled signals, and then determine whether there is a pulse feature within the sliding time window. Besides, the signal analysis apparatus 504 can determine that there is ROSC after defibrillation, if the number of the pulse waves in the sliding time window exceeds a threshold number, and/or the quality of a single pulse wave exceeds a threshold quality. The quality of the single pulse wave can be determined by its amplitude, width and shape, and the time duration of the sliding time window can be adaptively adjusted according to the frequency of the pulse wave.

Those skilled in the art can understand that all or partial steps of various methods in the embodiments can be completed by using a program to command relevant hardware products. This program can be stored in a readable storage medium of the computer, and the storage medium may include ROM, RAM, disk or optical disk.

The above-mentioned content gives further detailed descriptions on this disclosure in combination with specific embodiments. The specific implementation of this disclosure is not limited to these descriptions. For those skilled in the art, it is feasible to make several simple deductions or substitutions without deviating from the concept of this disclosure.

The invention claimed is:

1. A device for real-time recognition of restoration of spontaneous circulation (ROSC) in a cardio-pulmonary resuscitation (CPR) process, comprising:
   a signal acquisition apparatus comprising a sensor for blood oxygen saturation
   detection based upon light absorption and acquiring pulse oximetry waveform signals of a patient, at least one pulse oximetry waveform comprising a manual compression waveform signal and a spontaneous circulation waveform signal; and
   a signal analysis apparatus comprising a frequency-domain recognition logic for analyzing the pulse oximetry waveform signals in a frequency domain to identify a first frequency and a first amplitude for the manual compression waveform signal and a second frequency and a second amplitude for the spontaneous circulation waveform signal to determine whether there is ROSC in the CPR process by detecting time-varying features of spectral peaks of the signals including the second frequency and the second amplitude of the spontaneous circulation waveform signal in the frequency domain.

2. The device of claim 1, wherein: the signal analysis apparatus further comprises time-domain recognition logic, said time-domain recognition logic provided for determining whether there is ROSC in the CPR process by detecting a time envelope of the signals in the time domain.

3. The device of claim 2, wherein: the time-domain recognition logic determines that there is ROSC when continuous and regular envelope features are recognized.

4. The device of claim 1, wherein: the frequency-domain recognition logic determines that there is ROSC when spectral peaks are recognized continuously at different frequencies or significant amplitude change is recognized for spectral peaks within a certain period.

5. A restoration of spontaneous circulation (ROSC) recognition and post-ROSC circulation quality evaluation system, comprising:
   an ROSC recognition device and a post-ROSC circulation quality evaluation apparatus for evaluating post-ROSC circulation quality;
   the ROSC recognition device comprises:
   a signal acquisition apparatus comprising a sensor for blood oxygen saturation
   detection based upon light absorption and acquiring pulse oximetry waveform signals of a patient, at least one pulse oximetry waveform comprising a manual compression waveform signal and a spontaneous circulation waveform signal; and
   a signal analysis apparatus comprising a frequency-domain recognition logic for analyzing the pulse oximetry waveform signals in a frequency domain to identify a first frequency and a first amplitude for the manual compression waveform signal and a second frequency and a second amplitude for the spontaneous circulation waveform signal to determine whether there is ROSC in the CPR by detecting time-varying features of spectral peaks of the signals including the second frequency and the second amplitude of the spontaneous circulation waveform signal in the frequency domain.

6. The ROSC recognition and post-ROSC circulation quality evaluation system of claim 5, wherein the post- ROSC circulation quality evaluation apparatus evaluates the post-ROSC circulation quality based on variations of cardiac stroke volume within a certain period or based on variations of pulse rate.

7. The ROSC recognition and post-ROSC circulation quality evaluation system of claim 6, wherein after the ROSC recognition device has determined there is ROSC, the post-ROSC circulation quality evaluation apparatus calculates area characteristics of AC components of pulse signals sampled by the ROSC recognition device to evaluate the stroke volume variations under spontaneous cardiac rhythm to reflect post-ROSC circulation quality.

8. A restoration of spontaneous circulation (ROSC) feedback system in a cardio-pulmonary resuscitation (CPR) process, comprising:
   an ROSC recognition and post-ROSC circulation quality evaluation apparatus configured to recognize ROSC in the CPR process in real time from pulse oximetry waveform signals derived from a pulse oximeter, and to evaluate post-ROSC circulation quality, at least one pulse oximetry waveform signal comprising a manual compression waveform signal and a spontaneous circulation waveform signal, said apparatus being further configured to evaluate stability of the post-ROSC circulation quality, wherein the ROSC recognition and post-ROSC circulation quality evaluation apparatus comprises a frequency-domain recognition logic provided for analyzing the pulse oximetry waveform signals in a frequency domain to identify a first frequency and a first amplitude for the manual compression waveform signal and a second frequency and a second amplitude for the spontaneous circulation waveform signal to determine whether there is ROSC in the CPR process by detecting time-varying features of spectral peaks of the sampled signals including the second frequency and the second amplitude of the spontaneous circulation waveform signal in the frequency domain; and
   a CPR apparatus for providing compression output to a patient;
   wherein, upon detection of the ROSC, the ROSC recognition and post-ROSC circulation quality evaluation apparatus controls the CPR apparatus to stop compression output and start the post-ROSC circulation quality evaluation;
   wherein, when the post-ROSC circulation quality is evaluated to be unstable, the ROSC recognition and post-ROSC circulation quality evaluation apparatus controls the CPR apparatus to restart the compression output, and restarts the real-time recognition of ROSC.

9. The ROSC feedback system of claim 8, further comprising:
   a CPR quality evaluation apparatus for evaluating CPR quality;
   wherein, while the CPR apparatus is providing the compression output, the CPR apparatus interacts with the CPR quality evaluation apparatus so that the CPR quality evaluation apparatus recognizes CPR compression state and provides feedback to the CPR apparatus to achieve an optimal compression output.

10. The ROSC feedback system of claim 9, wherein:
    the ROSC recognition and post-ROSC circulation quality evaluation apparatus comprises frequency-domain recognition logic, said frequency-domain recognition logic determining whether there is ROSC in the CPR process by detecting time-varying features of spectral peaks of the sampled signals in the frequency domain.

11. The ROSC feedback system of claim 8, wherein: the frequency-domain recognition logic determines that there is ROSC when spectral peaks are recognized continuously at different frequencies or significant amplitude change is recognized for spectral peaks within a certain period.

12. The system of claim 8, wherein the ROSC recognition and post-ROSC circulation quality evaluation apparatus comprises further comprises time-domain recognition logic provided for determining whether there is ROSC in the CPR process by detecting time envelope features of sampled signals in the time domain.

13. The ROSC feedback system of claim 12, wherein: the time-domain recognition logic determines that there is ROSC when continuous and regular envelope features are recognized.

14. The ROSC feedback system of claim 12, wherein:
    the time-domain recognition logic determines that there is ROSC when continuous and regular envelope features are recognized, and determines whether there is ROSC in the CPR process by detecting time envelope features of sampled signals in the time domain.

15. A device for real-time recognition of restoration of spontaneous circulation (ROSC) in a cardio-pulmonary resuscitation (CPR) process, comprising:
    a signal acquisition apparatus comprising a sensor for blood oxygen saturation
       detection based upon light absorption and acquiring pulse oximetry waveform signals of a patient, at least one pulse oximetry waveform signal comprising a manual compression waveform signal and a spontaneous circulation waveform signal; and
    a signal analysis apparatus comprising a time-domain recognition logic provided for analyzing the pulse oximetry waveform signals in a frequency domain to identify a first frequency and a first amplitude for the manual compression waveform signal and a second frequency and a second amplitude for the spontaneous circulation waveform signal to determine whether there is ROSC in the CPR process by detecting time-varyinq features of spectral peaks of the sampled signals including the second frequency and the second amplitude of the spontaneous circulation waveform signal in the frequency domain;
    said time-domain recognition logic provided for determining whether there is ROSC in the CPR process by detecting a time envelope of the signals in the time domain and determining that there is ROSC when continuous and regular envelope features are recognized.

* * * * *